US012614451B2

(12) United States Patent
Sanchez

(10) Patent No.: US 12,614,451 B2
(45) Date of Patent: *Apr. 28, 2026

(54) LIGHT EMITTING DIODES AND DIODE ARRAYS FOR SMART RING VISUAL OUTPUT

(71) Applicant: QUANATA, LLC, San Francisco, CA (US)

(72) Inventor: Kenneth Jason Sanchez, San Francisco, CA (US)

(73) Assignee: QUANATA, LLC, San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/757,748

(22) Filed: Jun. 28, 2024

(65) Prior Publication Data

US 2024/0355201 A1 Oct. 24, 2024

Related U.S. Application Data

(63) Continuation of application No. 17/819,155, filed on Aug. 11, 2022, now Pat. No. 12,027,048, which is a (Continued)

(51) Int. Cl.
*G08G 1/0967* (2006.01)
*A61B 5/00* (2006.01)

(Continued)

(52) U.S. Cl.
CPC ......... *G08G 1/0967* (2013.01); *A61B 5/0002* (2013.01); *A61B 5/117* (2013.01);

(Continued)

(58) Field of Classification Search
CPC ...... G08G 1/0967; H04W 4/40; H04W 4/008; H04W 4/80; A61B 5/0002; A61B 5/117;

(Continued)

(56) References Cited

U.S. PATENT DOCUMENTS

| | | |
|---|---|---|
| 513,344 A | 1/1894 | Smith |
| 2,737,192 A | 3/1956 | Bieler |

(Continued)

FOREIGN PATENT DOCUMENTS

| | | |
|---|---|---|
| CN | 103109462 A | 5/2013 |
| CN | 104799509 | 7/2015 |

(Continued)

OTHER PUBLICATIONS

"How to find your ideal bedtime with the Oura app", available online at <https://web_archive.org/web/20191206205332/ https://ouraring.com/how-to-find-your-ideal-bedtime-with-the-oura-app/ 2019, 8 pages. 2019.

(Continued)

*Primary Examiner* — Brian A Zimmerman
*Assistant Examiner* — Anthony D Afrifa-Kyei
(74) *Attorney, Agent, or Firm* — BRYAN CAVE LEIGHTON PAISNER LLP

(57) ABSTRACT

A system for displaying information via a smart ring can include a ring band. The system for displaying information via a smart ring also can include at least one processor disposed within the ring band. The at least one processor disposed within the ring can be configured to identify a user of the smart ring. The at least one processor disposed within the ring further can be configured to analyze the data to identify a condition. The system for displaying information via a smart ring further can include a display disposed at least partially in, at least partially on, or coupled to the ring band and communicatively coupled to the processor. Furthermore, the at least one processor disposed within the ring can be configured to cause the display to present information indicative of the condition. Other embodiments are disclosed.

20 Claims, 6 Drawing Sheets

Related U.S. Application Data continuation of application No. 16/927,271, filed on Jul. 13, 2020, now Pat. No. 11,462,107.

(60) Provisional application No. 62/981,087, filed on Feb. 25, 2020, provisional application No. 62/877,391, filed on Jul. 23, 2019.

(51) Int. Cl.

| | |
|---|---|
| *A61B 5/117* | (2016.01) |
| *A61B 5/18* | (2006.01) |
| *B60K 35/10* | (2024.01) |
| *B60K 35/21* | (2024.01) |
| *B60K 35/22* | (2024.01) |
| *B60K 35/28* | (2024.01) |
| *B60K 35/60* | (2024.01) |
| *G06F 1/16* | (2006.01) |
| *G06F 3/01* | (2006.01) |
| *G09G 3/32* | (2016.01) |
| *H04W 4/40* | (2018.01) |
| *B60K 35/20* | (2024.01) |
| *B60K 35/25* | (2024.01) |
| *B60K 35/26* | (2024.01) |
| *B60K 35/29* | (2024.01) |
| *B60K 35/50* | (2024.01) |

(52) U.S. Cl.

CPC .............. *A61B 5/18* (2013.01); *A61B 5/4809* (2013.01); *A61B 5/4845* (2013.01); *A61B 5/681* (2013.01); *A61B 5/742* (2013.01); *B60K 35/10* (2024.01); *B60K 35/21* (2024.01); *B60K 35/22* (2024.01); *B60K 35/28* (2024.01); *B60K 35/60* (2024.01); *G06F 1/163* (2013.01); *G06F 1/1637* (2013.01); *G06F 3/014* (2013.01); *G09G 3/32* (2013.01); *H04W 4/40* (2018.02); *B60K 35/20* (2024.01); *B60K 35/25* (2024.01); *B60K 35/26* (2024.01); *B60K 35/29* (2024.01); *B60K 35/50* (2024.01); *G09G 2354/00* (2013.01)

(58) Field of Classification Search

CPC ....... A61B 5/18; A61B 5/4809; A61B 5/4845; A61B 5/681; A61B 5/742; G06F 1/163; G06F 1/1637; G06F 3/014; G06F 1/1635; G06F 1/1652; G06F 1/1686; G06F 1/1675; G06F 1/1694; G06F 1/1698; G06F 3/011; G06F 3/016; G06F 3/03547; G06F 3/04883; G06F 2203/04808; G09G 3/32; G09G 2354/00; G09G 3/14; G09G 2370/16; G09G 2380/02; G09G 2380/06; H04B 5/77; H04B 1/385; H04B 1/3816; H04B 1/3818; H04B 11/00; H04B 5/0062; H04B 2001/3861; H04M 1/0268; H04M 1/0264; H04M 2250/02; H04M 2250/04; H04M 2250/10; H04M 2250/12; H04M 1/72412; G06K 19/07762; G06K 19/00; G06K 19/06; G06K 19/067; G06K 19/07; G06K 19/077; G06K 19/07749; G06K 19/07758; G06K 19/0723; G06K 19/07701

See application file for complete search history.

(56) References Cited

U.S. PATENT DOCUMENTS

| | | | |
|---|---|---|---|
| 3,792,192 | A | 2/1974 | Plate |
| 4,012,629 | A | 3/1977 | Simms |
| 4,382,112 | A | 5/1983 | Betts et al. |
| 4,684,687 | A | 8/1987 | Breach et al. |
| 4,830,014 | A | 5/1989 | Goodman et al. |
| 4,880,304 | A | 11/1989 | Jaeb et al. |
| 5,135,220 | A | 8/1992 | Baldoni |
| 6,097,480 | A | 8/2000 | Kaplan |
| 6,154,658 | A | 11/2000 | Caci |
| 6,201,698 | B1 | 3/2001 | Hunter |
| 6,560,993 | B1 | 5/2003 | Bosque et al. |
| 6,608,562 | B1 | 8/2003 | Kimura et al. |
| 6,699,199 | B2 | 3/2004 | Asada et al. |
| 6,745,061 | B1 | 6/2004 | Hicks et al. |
| 6,792,044 | B2 | 9/2004 | Peng et al. |
| 6,800,693 | B2 | 10/2004 | Nishihara et al. |
| 6,803,391 | B2 | 10/2004 | Paglia et al. |
| 6,805,140 | B2 | 10/2004 | Velez, Jr. et al. |
| 6,894,628 | B2 | 5/2005 | Marpe et al. |
| 6,909,753 | B2 | 6/2005 | Meehan et al. |
| 6,959,116 | B2 | 10/2005 | Sezer et al. |
| 7,013,674 | B2 | 3/2006 | Kretchmer |
| 7,136,532 | B2 | 11/2006 | VanDer |
| 7,190,986 | B1 | 3/2007 | Hannula et al. |
| 7,227,894 | B2 | 6/2007 | Lin et al. |
| 7,275,172 | B2 | 9/2007 | Janzen et al. |
| 7,286,710 | B2 | 10/2007 | Marpe et al. |
| 7,468,036 | B1 | 12/2008 | Rulkov et al. |
| 7,500,697 | B2 | 3/2009 | Romack |
| 7,500,746 | B1 | 3/2009 | Howell et al. |
| 7,519,229 | B2 | 4/2009 | Wallace et al. |
| 7,689,437 | B1 | 3/2010 | Teller et al. |
| 7,872,444 | B2 | 1/2011 | Hamilton et al. |
| 8,031,172 | B2 | 10/2011 | Kruse et al. |
| 8,075,484 | B2 | 12/2011 | Moore-ede |
| 8,345,752 | B2 | 1/2013 | Lee et al. |
| 8,446,275 | B2 | 5/2013 | Utter, II |
| 8,554,297 | B2 | 10/2013 | Moon et al. |
| 8,570,273 | B1 | 10/2013 | Smith |
| 8,624,554 | B2 | 1/2014 | Ajagbe |
| 8,700,111 | B2 | 4/2014 | Leboeuf et al. |
| 8,954,135 | B2 | 2/2015 | Yuen et al. |
| 9,218,058 | B2 | 12/2015 | Bress et al. |
| 9,248,839 | B1 | 2/2016 | Tan |
| 9,248,938 | B2 | 2/2016 | Hopps |
| 9,265,310 | B2 | 2/2016 | Lam |
| 9,362,775 | B1 | 6/2016 | Jacobs |
| 9,420,260 | B2 | 8/2016 | McGregor et al. |
| 9,440,657 | B1 | 9/2016 | Fields et al. |
| 9,477,146 | B2 | 10/2016 | Xu et al. |
| 9,509,170 | B2 | 11/2016 | Wu |
| 9,628,707 | B2 | 4/2017 | Blum et al. |
| 9,660,488 | B2 | 5/2017 | Breedvelt-Schouten et al. |
| 9,696,690 | B2 | 7/2017 | Nguyen et al. |
| 9,711,060 | B1 | 7/2017 | Lusted et al. |
| 9,711,993 | B2 | 7/2017 | Kim |
| 9,717,949 | B1 | 8/2017 | Tran et al. |
| 9,733,700 | B2 | 8/2017 | Song et al. |
| 9,756,301 | B2 | 9/2017 | Li et al. |
| 9,841,331 | B2 | 12/2017 | Wood et al. |
| 9,847,020 | B2 | 12/2017 | Davis |
| 9,861,314 | B2 | 1/2018 | Haverinen et al. |
| 9,880,620 | B2 | 1/2018 | Kienzle et al. |
| 9,908,530 | B1 | 3/2018 | Fields et al. |
| 9,931,976 | B1 | 4/2018 | Terwilliger et al. |
| 9,955,286 | B2 | 4/2018 | Segal |
| 9,956,963 | B2 | 5/2018 | Vijaya Kumar et al. |
| 9,965,761 | B2 | 5/2018 | Elangovan et al. |
| 10,007,355 | B2 | 6/2018 | Schorsch et al. |
| 10,043,125 | B2 | 8/2018 | Park |
| 10,085,695 | B2 | 10/2018 | Ouwerkerk et al. |
| 10,099,608 | B2 | 10/2018 | Cuddihy et al. |
| 10,102,510 | B2 | 10/2018 | Yau et al. |
| 10,137,777 | B2 | 11/2018 | Lu et al. |
| 10,139,859 | B2 | 11/2018 | Von Badinski et al. |
| 10,252,016 | B2 | 4/2019 | Pedro et al. |
| 10,281,953 | B2 | 5/2019 | Bandinski |
| 10,303,867 | B2 | 5/2019 | Schröder |
| 10,315,557 | B2 | 6/2019 | Terwilliger et al. |
| 10,317,940 | B2 | 6/2019 | Eim et al. |
| 10,345,506 | B1 | 7/2019 | Lyu |

(56) References Cited

U.S. PATENT DOCUMENTS

| | | | |
|---|---|---|---|
| 10,359,846 B2 | 7/2019 | Priyantha et al. |
| 10,366,220 B2 | 7/2019 | Shapiro et al. |
| 10,377,386 B2 | 8/2019 | Richmond |
| 10,384,647 B2 | 8/2019 | Tayama |
| 10,396,584 B2 | 8/2019 | Madau et al. |
| 10,409,327 B2 | 9/2019 | Stotler |
| 10,444,834 B2 | 10/2019 | Vescovi et al. |
| 10,463,141 B2 | 11/2019 | Fitzgerald et al. |
| 10,509,994 B1 | 12/2019 | Huynh |
| 10,528,989 B1 | 1/2020 | Irey |
| 10,564,628 B2 | 2/2020 | Hargovan et al. |
| 10,629,175 B2 | 4/2020 | Yan et al. |
| 10,664,842 B1 | 5/2020 | Bermudez et al. |
| 10,679,296 B1 | 6/2020 | Devereaux et al. |
| 10,681,818 B1 | 6/2020 | Graber et al. |
| 10,693,872 B1 | 6/2020 | Larson et al. |
| 10,701,067 B1 | 6/2020 | Ziraknejad et al. |
| 10,703,204 B2 | 7/2020 | Hassan et al. |
| 10,709,339 B1 | 7/2020 | Lusted |
| 10,713,726 B1 | 7/2020 | Allen et al. |
| 10,745,032 B2 | 8/2020 | Scheggi |
| 10,762,183 B1 | 9/2020 | Charan et al. |
| 10,768,666 B2 | 9/2020 | Von Badinski et al. |
| 10,838,499 B2 | 11/2020 | Wang |
| 10,842,429 B2 | 11/2020 | Kinnunen et al. |
| 10,849,557 B2 | 12/2020 | Keating |
| 10,893,833 B2 | 1/2021 | Haverinen et al. |
| 10,944,745 B2 | 3/2021 | Kursun et al. |
| 11,056,242 B1 | 7/2021 | Jain et al. |
| 11,127,506 B1 | 9/2021 | Jain et al. |
| 11,227,060 B1 | 1/2022 | John et al. |
| 11,237,640 B2 | 2/2022 | Zhu et al. |
| 11,265,635 B2 | 3/2022 | Shankar |
| 11,271,290 B2 | 3/2022 | McLear et al. |
| 11,312,299 B1 | 4/2022 | Assam |
| 11,342,051 B1 | 5/2022 | Jain et al. |
| 11,456,080 B1 | 9/2022 | Jain et al. |
| 11,479,258 B1 | 10/2022 | Sanchez |
| 11,504,011 B1 | 11/2022 | Jain et al. |
| 11,599,147 B2 | 3/2023 | Von Badinski et al. |
| 11,601,424 B2 | 3/2023 | Fukuda |
| 11,637,511 B2 | 4/2023 | Sanchez |
| 11,714,494 B2 | 8/2023 | D'Amone et al. |
| 11,868,178 B2 | 1/2024 | Von Badinski et al. |
| 11,868,179 B2 | 1/2024 | Von Badinski et al. |
| 11,894,704 B2 | 2/2024 | Sanchez |
| 11,909,238 B1 | 2/2024 | Sanchez |
| 11,914,780 B2 | 2/2024 | Wang et al. |
| 11,923,791 B2 | 3/2024 | Sanchez |
| 11,984,742 B2 | 5/2024 | Sanchez |
| 11,990,954 B2 | 5/2024 | Kato et al. |
| 12,077,193 B1 | 9/2024 | Sanchez |
| 12,191,692 B2 | 1/2025 | Sanchez |
| 12,211,467 B2 | 1/2025 | Sanchez |
| 12,237,700 B2 | 2/2025 | Sanchez et al. |
| 2002/0042464 A1 | 4/2002 | Barclay et al. |
| 2002/0091568 A1 | 7/2002 | Kraft et al. |
| 2002/0121831 A1 | 9/2002 | Egawa et al. |
| 2003/0077064 A1 | 4/2003 | Katayama |
| 2003/0142065 A1 | 7/2003 | Pahlavan |
| 2004/0090210 A1 | 5/2004 | Becker et al. |
| 2004/0102551 A1 | 5/2004 | Sato et al. |
| 2004/0118592 A1 | 6/2004 | Pehlert |
| 2004/0145256 A1 | 7/2004 | Miekka |
| 2004/0160635 A1 | 8/2004 | Ikeda et al. |
| 2004/0200235 A1 | 10/2004 | Kretchmer |
| 2005/0012648 A1 | 1/2005 | Marpe et al. |
| 2005/0030205 A1 | 2/2005 | Konoshima et al. |
| 2005/0054941 A1 | 3/2005 | Ting et al. |
| 2005/0062454 A1 | 3/2005 | Raghunath et al. |
| 2005/0133248 A1 | 6/2005 | Easter |
| 2005/0162523 A1 | 7/2005 | Darrell et al. |
| 2005/0185060 A1 | 8/2005 | Neven, Sr. |
| 2005/0185843 A1 | 8/2005 | Kudoh |
| 2005/0185844 A1 | 8/2005 | Ono et al. |
| 2005/0230596 A1 | 10/2005 | Howell et al. |
| 2006/0002607 A1 | 1/2006 | Boncyk et al. |
| 2006/0069681 A1 | 3/2006 | Lauper |
| 2006/0080286 A1 | 4/2006 | Svendsen |
| 2006/0085477 A1 | 4/2006 | Phillips et al. |
| 2006/0089792 A1 | 4/2006 | Manber et al. |
| 2006/0211924 A1 | 9/2006 | Dalke et al. |
| 2006/0250043 A1 | 11/2006 | Chung |
| 2006/0271593 A1 | 11/2006 | De Mes et al. |
| 2007/0149222 A1 | 6/2007 | Hodko et al. |
| 2007/0159522 A1 | 7/2007 | Neven |
| 2007/0188626 A1 | 8/2007 | Squilla et al. |
| 2007/0200713 A1 | 8/2007 | Weber et al. |
| 2007/0223826 A1 | 9/2007 | Ridge et al. |
| 2008/0068559 A1 | 3/2008 | Howell et al. |
| 2008/0136587 A1 | 6/2008 | Orr |
| 2008/0174676 A1 | 7/2008 | Squilla et al. |
| 2008/0218684 A1 | 9/2008 | Howell et al. |
| 2008/0275309 A1 | 11/2008 | Stivoric et al. |
| 2009/0056703 A1 | 3/2009 | Mills et al. |
| 2010/0219989 A1 | 9/2010 | Asami et al. |
| 2011/0007035 A1 | 1/2011 | Shai |
| 2011/0080339 A1 | 4/2011 | Sun et al. |
| 2011/0224875 A1 | 9/2011 | Cuddihy et al. |
| 2012/0016245 A1 | 1/2012 | Niwa et al. |
| 2012/0075196 A1 | 3/2012 | Ashbrook et al. |
| 2012/0130203 A1 | 5/2012 | Stergiou et al. |
| 2012/0184367 A1 | 7/2012 | Parrott et al. |
| 2012/0218184 A1 | 8/2012 | Wissmar |
| 2012/0293107 A1 | 11/2012 | Ajagbe |
| 2012/0317024 A1 | 12/2012 | Rahman et al. |
| 2013/0106603 A1 | 5/2013 | Weast et al. |
| 2013/0211291 A1 | 8/2013 | Tran |
| 2013/0335213 A1 | 12/2013 | Sherony et al. |
| 2014/0091659 A1 | 4/2014 | Suzuki et al. |
| 2014/0107493 A1* | 4/2014 | Yuen .................... A61B 5/7455 |
| | | 600/479 |
| 2014/0118704 A1 | 5/2014 | Duelli et al. |
| 2014/0120983 A1 | 5/2014 | Lam |
| 2014/0187160 A1 | 7/2014 | Prencipe |
| 2014/0218529 A1 | 8/2014 | Mahmoud et al. |
| 2014/0238153 A1 | 8/2014 | Wood et al. |
| 2014/0240132 A1 | 8/2014 | Bychkov |
| 2014/0244009 A1 | 8/2014 | Mestas |
| 2014/0267024 A1 | 9/2014 | Keller et al. |
| 2014/0274203 A1 | 9/2014 | Ganong, III |
| 2014/0309849 A1 | 10/2014 | Ricci |
| 2014/0361934 A1 | 12/2014 | Ely et al. |
| 2014/0361945 A1 | 12/2014 | Misra et al. |
| 2015/0003693 A1 | 1/2015 | Baca et al. |
| 2015/0019266 A1 | 1/2015 | Stempora |
| 2015/0028996 A1 | 1/2015 | Agrafioti |
| 2015/0029089 A1 | 1/2015 | Kim |
| 2015/0046996 A1 | 2/2015 | Slaby et al. |
| 2015/0062086 A1 | 3/2015 | Nattukallingal |
| 2015/0065090 A1 | 3/2015 | Yeh |
| 2015/0098309 A1* | 4/2015 | Adams .................... G04F 10/00 |
| | | 368/10 |
| 2015/0124096 A1 | 5/2015 | Koravadi |
| 2015/0126824 A1 | 5/2015 | Leboeuf et al. |
| 2015/0133193 A1* | 5/2015 | Stotler ................ G06F 15/0216 |
| | | 455/557 |
| 2015/0158499 A1 | 6/2015 | Koravadi |
| 2015/0186092 A1 | 7/2015 | Francis et al. |
| 2015/0220109 A1 | 8/2015 | Von et al. |
| 2015/0277559 A1 | 10/2015 | Vescovi et al. |
| 2015/0287412 A1 | 10/2015 | Tang |
| 2015/0338926 A1 | 11/2015 | Park et al. |
| 2015/0352953 A1 | 12/2015 | Koravadi |
| 2016/0028267 A1 | 1/2016 | Lee et al. |
| 2016/0098530 A1 | 4/2016 | Dill et al. |
| 2016/0189149 A1 | 6/2016 | MacLaurin et al. |
| 2016/0192407 A1 | 6/2016 | Fyfe et al. |
| 2016/0207454 A1 | 7/2016 | Cuddihy |
| 2016/0226313 A1 | 8/2016 | Okubo |
| 2016/0236692 A1 | 8/2016 | Kleen et al. |
| 2016/0266606 A1 | 9/2016 | Ricci |
| 2016/0292563 A1 | 10/2016 | Park |
| 2016/0317060 A1 | 11/2016 | Connor |

(56) References Cited

U.S. PATENT DOCUMENTS

| | | |
|---|---|---|
| 2016/0334901 A1 | 11/2016 | Rihn |
| 2016/0336758 A1 | 11/2016 | Breedvelt-Schouten et al. |
| 2016/0350581 A1 | 12/2016 | Manuel et al. |
| 2016/0361032 A1 | 12/2016 | Carter et al. |
| 2017/0010677 A1 | 1/2017 | Roh et al. |
| 2017/0012925 A1 | 1/2017 | Tekin et al. |
| 2017/0024008 A1 | 1/2017 | Kienzle et al. |
| 2017/0026790 A1 | 1/2017 | Flitsch et al. |
| 2017/0042477 A1 | 2/2017 | Haverinen et al. |
| 2017/0053461 A1 | 2/2017 | Pal et al. |
| 2017/0057492 A1 | 3/2017 | Eddington et al. |
| 2017/0070078 A1 | 3/2017 | Hwang et al. |
| 2017/0075701 A1 | 3/2017 | Ricci et al. |
| 2017/0080952 A1 | 3/2017 | Gupta et al. |
| 2017/0090475 A1 | 3/2017 | Choi et al. |
| 2017/0109512 A1 | 4/2017 | Bower et al. |
| 2017/0129335 A1 | 5/2017 | Lu et al. |
| 2017/0131772 A1 | 5/2017 | Choi |
| 2017/0150255 A1 | 5/2017 | Wang et al. |
| 2017/0190121 A1 | 7/2017 | Aggarwal et al. |
| 2017/0192530 A1 | 7/2017 | Lee |
| 2017/0242428 A1 | 8/2017 | Pal et al. |
| 2017/0251967 A1 | 9/2017 | Premsukh |
| 2017/0336964 A1* | 11/2017 | Kim .................. G06F 3/0236 |
| 2017/0346635 A1 | 11/2017 | Gummeson et al. |
| 2017/0347895 A1 | 12/2017 | Wei et al. |
| 2017/0374074 A1 | 12/2017 | Stuntebeck |
| 2018/0025351 A1 | 1/2018 | Chen et al. |
| 2018/0025430 A1 | 1/2018 | Perl et al. |
| 2018/0032126 A1 | 2/2018 | Liu |
| 2018/0037228 A1 | 2/2018 | Biondo et al. |
| 2018/0039303 A1 | 2/2018 | Hashimoto |
| 2018/0052428 A1 | 2/2018 | Abramov |
| 2018/0054513 A1 | 2/2018 | Ma |
| 2018/0068105 A1 | 3/2018 | Shapiro et al. |
| 2018/0093606 A1* | 4/2018 | Terwilliger ............ H04W 4/46 |
| 2018/0093610 A1 | 4/2018 | Sun et al. |
| 2018/0093672 A1 | 4/2018 | Terwilliger et al. |
| 2018/0115797 A1 | 4/2018 | Wexler et al. |
| 2018/0120891 A1 | 5/2018 | Eim |
| 2018/0120892 A1 | 5/2018 | Von Badinski et al. |
| 2018/0123629 A1 | 5/2018 | Wetzig |
| 2018/0167200 A1 | 6/2018 | High et al. |
| 2018/0174457 A1 | 6/2018 | Taylor |
| 2018/0178712 A1 | 6/2018 | Terwilliger et al. |
| 2018/0229674 A1 | 8/2018 | Heinrich et al. |
| 2018/0256027 A1* | 9/2018 | Lacher ................ A61B 5/0002 |
| 2018/0257668 A1 | 9/2018 | Tonshal |
| 2018/0262505 A1 | 9/2018 | Ligatti |
| 2018/0292901 A1 | 10/2018 | Priyantha et al. |
| 2018/0300467 A1 | 10/2018 | Kwong et al. |
| 2018/0322957 A1 | 11/2018 | Dill et al. |
| 2019/0004325 A1 | 1/2019 | Connor |
| 2019/0049267 A1 | 2/2019 | Huang |
| 2019/0083022 A1 | 3/2019 | Huang |
| 2019/0131812 A1 | 5/2019 | Lee et al. |
| 2019/0155104 A1 | 5/2019 | Li et al. |
| 2019/0155385 A1 | 5/2019 | Lim et al. |
| 2019/0172289 A1 | 6/2019 | O'Toole et al. |
| 2019/0191998 A1 | 6/2019 | Heikenfeld et al. |
| 2019/0202464 A1 | 7/2019 | Mcgill |
| 2019/0213429 A1 | 7/2019 | Sicconi et al. |
| 2019/0229909 A1 | 7/2019 | Patel et al. |
| 2019/0230507 A1 | 7/2019 | Li et al. |
| 2019/0265868 A1 | 8/2019 | Penilla et al. |
| 2019/0286805 A1 | 9/2019 | Law et al. |
| 2019/0287083 A1 | 9/2019 | Wurmfeld et al. |
| 2019/0295440 A1 | 9/2019 | Hadad |
| 2019/0298173 A1 | 10/2019 | Lawrence et al. |
| 2019/0298265 A1 | 10/2019 | Keating |
| 2019/0313967 A1 | 10/2019 | Lee |
| 2019/0332140 A1 | 10/2019 | Wang et al. |
| 2019/0332787 A1 | 10/2019 | Graf et al. |
| 2019/0342329 A1 | 11/2019 | Turgeman |
| 2019/0357834 A1 | 11/2019 | Aarts et al. |

| | | |
|---|---|---|
| 2020/0001895 A1 | 1/2020 | Scheggi |
| 2020/0005791 A1 | 1/2020 | Rakshit et al. |
| 2020/0062276 A1 | 2/2020 | Yuan et al. |
| 2020/0070840 A1 | 3/2020 | Gunaratne |
| 2020/0142497 A1 | 5/2020 | Zhu |
| 2020/0159896 A1 | 5/2020 | Shapiro et al. |
| 2020/0218238 A1 | 7/2020 | Wang |
| 2020/0356652 A1 | 11/2020 | Yamaguchi et al. |
| 2020/0391696 A1* | 12/2020 | Kato ..................... G06V 40/10 |
| 2020/0401183 A1 | 12/2020 | Von Badinski et al. |
| 2021/0019731 A1 | 1/2021 | Rule et al. |
| 2021/0029112 A1 | 1/2021 | Palle et al. |
| 2021/0058692 A1 | 2/2021 | Shankar |
| 2021/0197849 A1 | 7/2021 | Tsuji |
| 2021/0382684 A1 | 12/2021 | Hachiya et al. |
| 2022/0083149 A1 | 3/2022 | Keller et al. |
| 2022/0233142 A1 | 7/2022 | Hasan et al. |
| 2022/0320899 A1 | 10/2022 | Sanchez et al. |
| 2023/0027131 A1 | 1/2023 | Sanchez et al. |
| 2023/0225671 A1 | 7/2023 | Kosman et al. |

FOREIGN PATENT DOCUMENTS

| | | | |
|---|---|---|---|
| CN | 105960196 | | 9/2016 |
| CN | 106360895 | | 2/2017 |
| CN | 206213423 | | 6/2017 |
| CN | 206333477 | | 7/2017 |
| CN | 206371611 | | 8/2017 |
| CN | 107139933 | | 9/2017 |
| CN | 107260139 | | 10/2017 |
| CN | 104157116 | A | 12/2017 |
| CN | 105006103 | B | 4/2018 |
| CN | 105841851 | | 8/2018 |
| CN | 108900691 | | 11/2018 |
| CN | 108926081 | | 12/2018 |
| DE | 10201301233399 | | 7/2013 |
| DE | 102015006677 | | 11/2016 |
| DE | 102019116618 | | 12/2020 |
| EP | 1223191 | A1 | 7/2002 |
| EP | 1384752 | A1 | 1/2004 |
| EP | 2281205 | A1 | 2/2011 |
| EP | 2581856 | | 4/2013 |
| JP | 200879676 | | 4/2008 |
| KR | 20110012229 | | 2/2011 |
| KR | 20170013067 | | 2/2017 |
| KR | 1020170087113 | | 7/2017 |
| KR | 101835991 | B1 | 4/2018 |
| WO | 2001017421 | | 3/2001 |
| WO | 2005114476 | A1 | 12/2005 |
| WO | 2005124594 | A1 | 12/2005 |
| WO | 2008008714 | A1 | 1/2008 |
| WO | 2011132009 | A2 | 4/2011 |
| WO | 2015077418 | | 5/2015 |
| WO | 2017136940 | | 8/2017 |
| WO | 2018000396 | | 1/2018 |
| WO | 2018048563 | A1 | 3/2018 |
| WO | 2018154341 | | 8/2018 |
| WO | 2018164632 | | 9/2018 |
| WO | 2018204811 | | 11/2018 |
| WO | 2019082095 | | 5/2019 |
| WO | 2019140528 | | 7/2019 |
| WO | 2019180626 | | 9/2019 |

OTHER PUBLICATIONS

"Vauxhall/Opel In-Car Wireless Charging", retrieved from <https://www.air-charge.com/aircharge-for-business/automotive/vauxhall-wireless-charging>, Oct. 2019, 4 pages. Oct. 2019.

"Wireless charging for smart ring/pointing devices" available online at <http://www.humavox.comismt_product/wireless-charging-for-smart-ringpointing-devices/>, Oct. 2019, 3 pages Oct. 2019.

Adafruit, p. 1-2, available at: https://adafruit.com/product/2806, published Jun. 2019 (Year: 2019) 2019.

adafruit.com, "RFID/NFC Smart Ring—Size 12—NTAG213," accessed at https://web.archive.org/web/20190605061438/https://www.adafruit.com/product/2806, publication Jun. 5, 2019 Jun. 5, 2019.

(56)    References Cited

OTHER PUBLICATIONS

ASU projection wearable: Live tomorrow today (world first launch @ CES 2016). (Dec. 2015). ASU Tech, YouTube. Retrieved from https://www.youtube.com/watch?v=Wdb50-D7YOY Dec. 2016.

Brownell, L., "Low-cost wearables manufactured by hybrid 3D printing. Wyss Institute, Harvard," Retrieved from https://wyss. harvard.edu/news/low-cost-wearables-manufactured-by-hybrid-3d-printingt, Sep. 6, 2017, pp. 11 Sep. 6, 2017.

Cetin, C., "Design, testing and implementation of a new authentication method using multiple devices," Graduate Theses and Dissertations, University of South Florida Scholar Commons. Retrieved from http://scholarcommons.usf.edu/etd/5660, Jan. 2015, pp. 61 Jan. 2015.

Charles Q. Choi, "Low Battery? New Tech Lets You Wirelessly Share Power", available online at <https://www_livescience.com/54790-new-tech-enables-wireless-charging_html>, May 19, 2016, 9 pages May 19, 2016.

Chen, X. A_, et al., "Encore: 3D printed augmentation of everyday objects with printed-over, affixed and interlocked attachments," Nov. 5, 2015, pp. 73-82 Nov. 5, 2015.

Chen, X. A_, et al., "Reprise: A design tool for specifying, generating, and customizing 3D printable adaptations on everyday objects," Oct. 16, 2016, pp. 29-39 Oct. 16, 2016.

E-Senses, "Personal vitamin D, sunlight and daylight coach", available online at <https://e-senses.com/>, 2019, 5 pages 2019.

Google translation of KR20170087113A (Year: 2016) 2016.

Hipolite, W., "The 3D printed 0 Bluetooth Ring is one of the tiniest personal computers you will ever see," 3DPrint.com. Retrieved from https://3dprint.com/34627/o-bluetooth-ring-3d-printed/, Jan. 2015, pp. 5 Jan. 2015.

https://en.wikipedia.org/w/index.php?title=Ring_size&oldid=891328817 2019.

Hussain Almossawi, "This smart ring aims to provide better lives for people with sickle cell disease", retrieved from < Dhttps://www.core77.com/projects/82131/This-Smart-Ring-Aims-to-Provide-Better-Lives-for-People-with-Sickle-Cell-2021, 9 pages 2021.

Je et al., "PokeRing: Notifications by poking around the finger", Proceedings of the 2018 CHI Conference on Human Factors in Computing Systems—CHI'18, 2018, paper 542, pp. 1-10 2018.

Katharine Schwab, "Orii, the ring that turns your finger into a phone, is here", available online at < https://www_fastcompany_com/90399237/orii-the-ring-that-turns-your-finger-into-a-phone-is-here >, 2019, 4 pages 2019.

Laput et al., "Skin buttons: cheap, small, low-powered and clickable fixed-icon laser projectors," UIST '14: Proceedings of the 27th Annual ACM Symposium on User Interface Software and Technology, pp. 389-394 Oct. 2014.

Magno et al., "Self-sustainable smart ring for long-term monitoring of blood oxygenation", IEEE Access, 2019, pp. 115400-115408 2019.

Mahmud et al., Wearable technology for drug abuse detection: A survey of recent advancements, Smart Health, vol. 13, Aug. 2019, 100062 Aug. 2019.

Margaret, "The Orb: A Bluetooth headset that turns into a ring", Gadgets, BornRich, Jun. 2013, available online at <http://www.bomrich.com/the-orb-a-bluetooth-headset-that-tums-into-a-ring_html > Jun. 2013.

Mario, https://www.smartringnews.com/posts/smart-ring-vs-smartwatch-which-is-the-best-fitness-and-activity-tracker 2014.

Nassi et al., "Virtual breathalyzer", Department of Software and Information Systems Engineering, Ben-Gurion University of the Negev, Israel, 2016, 10 pages 2016.

Neev Kiran, "SkinnySensor: Enabling Battery-Less Wearable Sensors via Intrabody Power Transfer", Masters Theses 694, University of Massachusetts Amherst, 2018, 63 pages 2018.

Nerd-Fu, "Push present", Delicious Juice Dot Com, Apr. 2015, available online at < https://blog_deliciousjuice_com/2015/04/ > Apr. 2015.

Pablo E SuArez, "NXT Ring—Your Digital-self at Hand", available online at <https://www_youtube.com/watch?v=9w7uxDHs7NY>, uploaded on Jun. 21, 2019, 2 pages Jun. 21, 2019.

Roumen et al., "NotiRing: A comparative study of notification channels for wearable interactive rings", Proceedings of the 33rd Annual ACM Conference on Human Factors in Computing Systems—CHI'15, 2015, pp. 2497-2500 2015.

Sarah Jacobsson Purewal, "Ringly review: The smart ring that could be sexier", available online at <https://www_macworld_com/article/227133/ringly-review-the-smart-ring-that-could-be-sexier.html>, 2016, 10 pages 2016.

Schwab, K, "This startup wants to kill passwords-and replace them with jewelry. Fast Company," Retrieved from https://www.fastcompany.com/90254843/this-startup-wants-to-kill-passwords-and-replace-them-with-jewelry, (Oct. 2018), pp. 7 Oct. 2018.

Seung et al., "Nanopatterned Textile-Based Wearable Triboelectric Nanogenerator", ACS Nano, vol. 9, 2015, pp. 3501-3509 2015.

Shane McGlaun, "Geek builds Bluetooth Smart Ring with OLED display", available online at <https://www_slashgear.com/geek-builds-bluetooth-smart-ring-with-oled-display-02361383/>, 2015, 6 pages 2015.

Sperlazza, e tested four sleep tracker apps and wearables: Here are the best ones, available online at <https://www_bulletproof_com/sleep/tech/best-sleep-tracker-apps/>, 2019, 18 pages 2019.

Turunen, "Smart ring for stress control and self-understanding", available online at <https://slowfinland.fi/en/smart-ring-for-stress-control-and-self-understanding/>, 2017, 9 pages 2017.

Woochit Tech (2017). New smart ring monitors UV exposure [video file]. Retrieved from https://www.youtube.com/watch?v=4YvkioTZxjU, 3 pgs 2017.

Worgan et al., "Garment level power distribution for wearables using inductive power transfer," 9th International Conference on Human System Interactions (HSI), 2016, pp. 277-283 2016.

Xiao et al., "LumiWatch: On-arm projected graphics and touch input," Proceedings of the 2018 CHI Conference on Human Factors in Computing Systems—CHI'18, 2018, pp. 1-11 2018.

Zhu et al., "Developing a driving fatigue detection system using physiological sensors," Proceedings of the 29th Australian Conference on Computer-Human Interaction—OZCHI'17, 2017, pp. 566-570 2017.

Zhu, M., et al., "Fluidic fabric muscle sheets for wearable and soft robotics," Retrieved from https://arxiv.org/pdf/1903.08253.pdf, Mar. 2019, pp. 32 Mar. 2019.

"The Oura App | Oura Ring", available online at <https://web.archive.org/web/20191019192921/https://ouraring.com/introducing-the-new-oura-app/>, 6 pages Oct. 29, 2019.

"Get the Technical Specs of Oura Ring | Oura Ring", available online at <https://web.archive.org/web/2019129014439/ https://ouraring.com/tech-specs/>, 3 pages Jan. 29, 2019.

"Learn how the Oura ring works | Go inside | Oura Ring", available online at <https://web.archive.org/web/20181127193557/https://ouraring.com/how-oura-works/>, 5 pages Nov. 27, 2018.

Oura Ring Generation 1 User Manual, available online at < https://fccid.io/2AD7V-OURARING15001/User-Manual/User-Manual-2844448.pdf>, 8 pages Nov. 24, 2015.

Oura Ring Generation 2 User Manual, available online at < https://fccid.io/2AD7V-OURA1801/User-Manual/User-manual-v2-3856414.pdf>, 13 pages Mar. 27, 2018.

Oura ring. Improve sleep. Perform better. by OURA—Kickstarter, available online at <https://web.archive.org/web/20160427015852/https://www.kickstarter.com/projects/oura/oura-ring-improve-sleep-perform-better/description>, 27 pages Apr. 27, 2016.

OURA Ring review—The Gadgeteer, available online at < https://the-gadgeteer.com/2017/08/11/oura-ring-review/> 16 pages Aug. 11, 2017.

Important Information Please Read JZ50-0148 user manual available with gen 2 ring purchase, 4 pages May 13, 2019.

Important Information Please Read JZ50-0149 user manual available with gen 2 ring purchase, 4 pages May 13, 2019.

Oura Ring | Sleep Tracker and Smart Ring with a Heart Rate Monitor, available online at <https://web.archive.org/web/20180709050831/https://ouraring.com/>, 12 pages Jul. 9, 2018.

(56) References Cited

OTHER PUBLICATIONS

Introducing the New Oura Ring Generation 3—The Pulse Blog, available online at <https://ouraring.com/blog/oura-generation2-vs-generation3/>, 3 pages Oct. 26, 2021.

Oura Ring 2 Teardown: Inside the NBA's COVID-19-Detecting Smart Ring, available at < https://www.youtube.com/watch?v=BwA1hmSVgVY> Jul. 9, 2020 (script).

Oura Ring 2 Teardown: Inside the NBA's COVID-19-Detecting Smart Ring, available at < https://www.youtube.com/watch?v=BwA1hmSVgVY> Jul. 9, 2020 (screenshots).

Rhee et al., (2000). Artifact-resistant, power-efficient design of finger-ring plethysmographic sensors. I. Design and analysis. 4. 2792-2795 vol. 4. 10.1109/IEMBS.2000.901443. 2000.

Rhee et al., (2000). Artifact-resistant, power-efficient design of finger-ring plethysmographic sensors. II. Prototyping and benchmarking. 4. 2796-2799 vol. 4. 10.1109/IEMBS.2000.901444. 2000.

Dynamic drinkware-type analysis for mestas.

Liu et al., (2009). UWave: Accelerometer-based personalized gesture recognition and its applications. Pervasive and Mobile Computing. 5. 657-675. 10.1016/j.pmcj.2009.07.007. 2009.

Trigueiros et al., (2019). A comparison of machine learning algorithms applied to hand gesture recognition. 2019.

Castaneda et al., (2018), Int J Biosens Bioelectron. 2018, "A review on wearable photoplethysmography sensors and their potential future applications in health care"; 4(4):195-202. doi:10.15406/ijbsbe.2018.04.00125. 2018.

Mendelson et al., (2006). A Wearable Reflectance Pulse Oximeter for Remote Physiological Monitoring. Conference proceedings : . . . Annual International Conference of the IEEE Engineering in Medicine and Biology Society. IEEE Engineering in Medicine and Biology Society. Conference. 1. 912-5. 10.1109/IEMBS.2006.260137. 2006.

Smiley, S., Active RFID vs. Passive RFID: What's the Difference? https://www.atlasrfidstore.com/rfid-insider/active-rfid-vs-passive-rfid/?srsltid=AfmBOoqhNhYwPPUSENIXB8LarZMm3TVQ4ugn4nTNUhfpy-9yYC_j0wdm Mar. 2016.

Lawton, G., (2022). Active vs. passive RFID tags: Which to choose: TechTarget. Retrieved from: https://www.techtarget.com/searcherp/tip/Active-vs-passive-RFID-tags-Which-to-choose Nov. 2022.

Amma et al., (2010). Airwriting recognition using wearable motion sensors. ACM International Conference Proceeding Series. 10. 10.1145/1785455.1785465. 2010.

Zhou et al., (2012). Analysis and Selection of Features for Gesture Recognition Based on a Micro Wearable Device. International Journal of Advanced Computer Science and Applications. 3. 10.14569/IJACSA.2012.030101. 2012.

Rhee et al., (2001). Artifact-resistant power-efficient design of finger-ring plethysmographic sensors. IEEE transactions on biomedical engineering. 48. 795-805. 10.1109/10.930904. 2001.

Ying et al., (2007). Automatic Step Detection in the Accelerometer Signal. 10.1007/978-3-540-70994-7_14. 2007.

100 Best Inventions of 2020 https://time.com/collection/best-inventions-2020/ 2020.

Clark, B. A.. "Color in Sunglass Lenses*." Optometry and Vision Science 46 (1969): 825-840. 1969.

Rhee, Sokwoo. (2006). Design and analysis of artifact-resistive finger photoplethysmographic sensors for vital sign monitoring/. 2006.

Webster, J.G., Design of pulse oximeters Webster—Institute of Physics Publishing—2003 2003.

Park et al., (2011). E-gesture: A collaborative architecture for energy-efficient gesture recognition with hand-worn sensor and mobile devices. SenSys 2011—Proceedings of the 9th ACM Conference on Embedded Networked Sensor Systems. 359-360. 10.1145/1999995.2000034. 2011.

Teh et al., (2000). Embedding of electronics within thermoplastic polymers using injection moulding technique. Filtration Industry Analyst. 10-18. 10.1109/IEMT.2000.910703. 2000.

Sakai, Tadamoto. (1993). Encapsulation process for electronic devices using injection molding method. Advances in Polymer Technology. 12. 61-71. 10.1002/adv.1993.060120106. 1993.

Ardebili et al.—William Andrew—2019. Encapsulation technologies for electronic applications 2019.

Au, Lawrence et al., (2009). Episodic Sampling: Towards Energy-efficient Patient Monitoring with Wearable Sensors. Conference proceedings : . . . Annual International Conference of the IEEE Engineering in Medicine and Biology Society. IEEE Engineering in Medicine and Biology Society. Conference. 2009. 6901-5. 10.1109/IEMBS.2009.5333615. 2009.

Silverman, A. (2002). Fifty Years of Glass-Making. Industrial & Engineering Chemistry. 18. 10.1021/ie50201a004. 2002.

Petropoulos et al., (2012). Flexible PCB-MEMS flow sensor. Procedia Engineering. 47. 236-239. 10.1016/j.proeng.2012.09.127. 2012.

Schlömer et al., (2008). Gesture Recognition with a Wii Controller. First publ. in: Proceedings of the 2nd International Conference on Tangible and Embedded Interaction 2008, Bonn, Germany, Feb. 18-20, 2008, pp. 11-14. 10.1145/1347390.1347395. 2008.

Rekimoto, J. (2001). GestureWrist and GesturePad: unobtrusive wearable interactiondevices. International Symposium on Wearable Computers, Digest of Papers. 21-27. 10.1109/ISWC.2001.962092. 2001.

Guidelines to Enhancing the Heart-Rate Monitoring Performance of Biosensing Wearables https://www.analog.com/en/resources/technical-articles/guidelines-to-enhancing-the-heartrate-monitoring-performance-of-biosensing-wearables.html 2019.

Krzyanowski, J. "How are PCB's made? A Beginner's Guide to the PCB Manufacturing Process" Retrieved from Knowledge zone https://vectorbluehub.com/how-are-pcbs-made 2023. Ciofu, et al., (2013) Njection and Micro Injection of Polymeric . . . First edition of the International Scientific Conference Modern Technologies in Machine Manufacturing Technology TMCM ISSN 2067-3604, vol. V, No. 1/2013https://modtech.ro/international-journal/vol. 5no12013/Ciofu_Ciprian_1.pdf 2013.

Ross, R.J.. (2004). LCP injection molded packages—keys to JEDEC 1 performance. 1807-1811 vol. 2. 10.1109/ECTC.2004.1320364. 2004.

Murphy, K. (2012) Machine learning: a probabilistic perspective 2012.

Olofson et al., Machining of titanium alloys—Battelle Memorial Institute, Defense Metals Information Center—1965 1965.

Asada et al., "Mobile monitoring with wearable photoplethysmographic biosensors," in IEEE Engineering in Medicine and Biology Magazine, vol. 22, No. 3, pp. 28-40, May-Jun. 2003, doi: 10.1109/MEMB.2003.1213624 2003.

Chen et al., (2009). Monitoring Human Movements at Home Using Wearable Wireless Sensors. Engineering Faculty Presentations 2009.

On the Heels of 1 Million Rings Sold, Oura Now Valued at $2.55 Billion https://www.businesswire.com/news/home/20220405006108/en/On-the-Heels-of-1-Million-Rings-Sold-Oura-Now-Valued-at-2.55-Billion#:~:text=SAN%20FRANCISCO%2D%2D(BUSINESS%20WIRE,of%20selling%201%2C000%2C000%20Oura%20Rings, Apr. 2022.

Lister et al., (2018) Optical properties of human skin https://www.spiedigitallibrary.org/journals/journal-of-biomedical-optics/volume-17/issue-9/090901/Optical-properties-of-human-skin/10.1117/1.JBO.17.9.090901.full 2018.

Uchino et al., (2000). Prediction of Optical Properties of Commercial Soda-Lime-Silicate Glasses Containing Iron. Journal of Non-Crystalline Solids. 261. 72-78. 10.1016/S0022-3093(99)00617-1. 2000.

Lawrence et al., (1989) "Pulse Oximetry" Anesthesiology: The journal of the American Society of Anesthesiologists, Inc. vol. 70 No. 1 1989.

Konig et al., (1998) "Reflectance Pulse Oximetry-Principles and obstetric application in the zurich system" Journal of Clinical Monitoring and Computing vol. 14 No. 6 p. 3-6 1998.

Hill et al., (2024) The Best Smart Ring to Rule Them All Retrieved from: https://www.wired.com/gallery/best-smartrings/ 2024.

Kaltenbach, F. (2004). Translucent Materials: Glass, Plastics, Metals 2004.

(56)                              References Cited

OTHER PUBLICATIONS

Zhu et al., (2011). Wearable Sensor-Based Hand Gesture and Daily Activity Recognition for Robot-Assisted Living. IEEE Transactions on Systems, Man, and Cybernetics, Part A. 41. 569-573. 10.1109/TSMCA.2010.2093883. 2011.

Stables et al., (2022). Why the Oura Ring Gen 3 was our wearable of the year. Retrieved from: https://www.wareable.com/wearable-tech/why-the-oura-ring-3-was-our-wearable-of-the-year-2022 2022.

Sun et al., (2013). Wireless Power Transfer for Medical Microsystems. 10.1007/978-1-4614-7702-0. 2013.

U.S. Appl. No. 61/768,279 2013.

Sleep Lab validation of a wellness ring detecting sleep patterns based on photoplethysmogram, actigraphy and body temperature published Feb. 9, 2016, to Kinnunen (Year: 2016) 2016.

* cited by examiner

LIGHT EMITTING DIODES AND DIODE ARRAYS FOR SMART RING VISUAL OUTPUT

CROSS-REFERENCES TO RELATED APPLICATIONS

This application is a continuation of U.S. Non-Provisional patent application Ser. No. 17/819,155 filed on Aug. 11, 2022 which is a continuation of U.S. Non-Provisional patent application Ser. No. 16/927,271 filed on Jul. 13, 2020, which claims priority to U.S. Provisional Patent Application No. 62/877,391 filed on Jul. 23, 2019 and U.S. Provisional Patent Application No. 62/981,087 filed on Feb. 25, 2020, all of which are incorporated by reference herein for all purposes.

FIELD OF THE DISCLOSURE

The present disclosure generally relates to implementations of smart ring wearable devices and, more particularly, to methods and devices for displaying information indicative of driving conditions to a driver via smart ring wearable devices.

BACKGROUND

Information pertaining to driving conditions of a vehicle and/or driver are valuable for navigation of the vehicle, ensuring safe operation of the vehicle, and lawful operation of the vehicle. Typically, operators of vehicles are provided, via a console display within the vehicle, with a limited amount of information pertaining to the vehicle (such as a speed of the vehicle or operational statuses of various elements of the vehicle such as the motor, oil levels, heat levels, etc.). In typical vehicles, information provided by the vehicle to an operator of a vehicle is typically limited to the operational statuses of the vehicle itself.

BRIEF SUMMARY

As disclosed herein, a smart ring device is configured for displaying information indicative of driving conditions to a driver. The smart ring device allows for the presentation of a multitude of different factors and conditions to a driver of a vehicle (e.g., a wearer of the smart ring) during operation of a vehicle. One benefit of the smart ring device is that the smart ring may measure biometrics of the driver and display indications of the biometrics such as a heart rate, blood pressure, blood-oxygen level, etc. Further, based at least in part upon the biometric information, the smart ring may provide indications to a driver of an operational state of the driver (e.g., a weariness level of a driver, an inebriation level, etc.) to indicate a potential risk of hazardous driving of the driver. The smart ring may be easily worn by a user of the smart ring throughout the user's day, and/or overnight, allowing the smart ring to track sleeping habits and physical exertion allowing for the smart ring to more accurately determine physical states of the wearer of the smart ring, compared to other user associated cellular devices such as a cell phone or step tracker. The state of the wearer may be determined over a period of time, for example the smart ring may determine that the wearer has had a lack of sleep or rest recently and the smart ring may display an indication of a lack of sleep to the wearer at a later time when the wearer of the smart ring is operating a vehicle. The smart ring may provide indications of a state of a driver that is the result of the state of the wearer over the last few hours, days, etc. Additionally, the smart ring may display to a driver indications of environmental conditions, operating conditions of the vehicle, conditions of other drivers, conditions of other vehicles, or may display driving risk levels based at least in part upon any of the conditions, or combinations of conditions.

Conventional vehicle console displays are large and need a driver to gaze at the console to observe information presented by the console, or to make selections on the console, which could be hazardous when driving in certain conditions (e.g., congested traffic, during rain or inclement weather, along a ridge or mountainside, etc.) Additionally, cellular devices, such as cell phones or tablets, associated with a user needs the driver to look at the screen or operate the device, which is illegal in some regions. The smart ring device can provide indications to a driver without the driver having to remove any hands from a steering wheel of the vehicle, or having to shift their gaze to a central console, which can reduce the risk of hazardous driving, and/or unlawful driving. Additionally, the display methods of the smart ring device have low-power needs compared to conventional display technologies.

This summary is provided to introduce a selection of concepts that are further described below in the detailed description. Certain embodiments may include features and advantages not described in this summary. Further, certain embodiments may omit one or more (or all) of the features and advantages described in this summary.

In an embodiment, a system for displaying information indicative of driving conditions to a driver via a smart ring device includes a ring band having a plurality of surfaces including an inner surface, an outer surface, a first side surface, and a second side surface. The smart ring further includes a processor, configured to obtain data from a communication module disposed within the ring band or from one or more sensors disposed within the ring band, the data being representative of information indicative of the one or more driving conditions. The smart ring also includes a light emitting diode (LED) display disposed on at least one of the plurality of surfaces, configured to present, to a user of the smart ring device, information indicative of one or more driving conditions.

The system may further include a power source disposed within the ring band configured to power the smart ring device, and a memory to store computer-executable instructions. The computer executable instructions may cause the processor to obtain information indicative of the one or more driving conditions, and to control the LED display to cause the LED display to display visual indicia indicative of the one or more driving conditions.

The communication module may be configured to provide communications between the smart ring device and external devices and systems. The smart ring device may communicate, via the communication module, with a mobile device associated with the driver of a vehicle, wherein the mobile device is configured to obtain information from sensors of the vehicle.

The system may further include biometric sensors configured to monitor biometrics of the wearer of the smart ring, and further configured to communicate, via the communication module, biometric information to a mobile device associated with the driver of the vehicle.

The information indicative of driving conditions may be indicative of a speed of a vehicle, an acceleration of a vehicle, a current weather condition, a sleepiness condition of a driver, a cognoscente condition of a driver, an inebriation condition of a driver, an operational status of a vehicle, and/or biometric information of a wearer of the smart ring device.

In another embodiment, a system for displaying information via a smart ring can include a ring band. The system for displaying information via a smart ring also can include at least one processor disposed within the ring band. The system for displaying information via a smart ring further can include a display disposed at least partially in, at least partially on, or coupled to the ring band and communicatively coupled to the processor. The at least one processor disposed within the ring band can be configured to identify a user of the smart ring. The at least one processor disposed within the ring band also can be configured to receive data from a communication module within the ring band. The at least one processor disposed within the ring further can be configured to receive data from a sensor within the ring band. The at least one processor disposed within the ring further can be configured to analyze the data to identify a condition. The at least one processor further can be configured to cause the display to present information indicative of the condition.

In another embodiment, a method of displaying information via a smart ring can include identifying a user of the smart ring by at least one processor disposed within a ring band of the smart ring. The method of displaying information via a smart ring also can include receiving data from a communication module within the ring band by at least one processor disposed within a ring band of the smart ring. The method of displaying information via a smart ring further can include receiving data from a sensor within the ring band by at least one processor disposed within a ring band of the smart ring. The method of displaying information via a smart ring further can include analyzing the data to identify a condition by at least one processor disposed within a ring band of the smart ring. The method of displaying information via a smart ring further can include presenting the information indicative of the condition via a display disposed at least partially in, at least partially on, or coupled to the ring band and communicatively coupled to the at least one processor.

In another embodiment, one or more non-transitory computer-readable media comprising computing instructions that, when executed on one or more processors, cause the one or more processors to perform operations. The operations can be performed by at least one processor disposed within a ring band of the smart ring. The operations also can include presenting information indicative of the condition via a display disposed at least partially in, at least partially on, or coupled to the ring band and communicatively coupled to the at least one processor. The operations performed by the at least one processor disposed within a ring band of the smart ring can include identifying a user of the smart ring. The operations performed by the at least one processor disposed within a ring band of the smart ring also can include receiving data from a communication module within the ring band. The operations performed by the at least one processor disposed within a ring band of the smart ring further can include receiving data from a sensor within the ring band. The operations performed by the at least one processor disposed within a ring band of the smart ring further can include analyzing the data to identify a condition.

Depending upon the embodiment, one or more benefits may be achieved. These benefits and various additional objects, features and advantages of the present disclosure can be fully appreciated with reference to the detailed description and accompanying drawings that follow.

DETAILED DESCRIPTION

Figure 1:
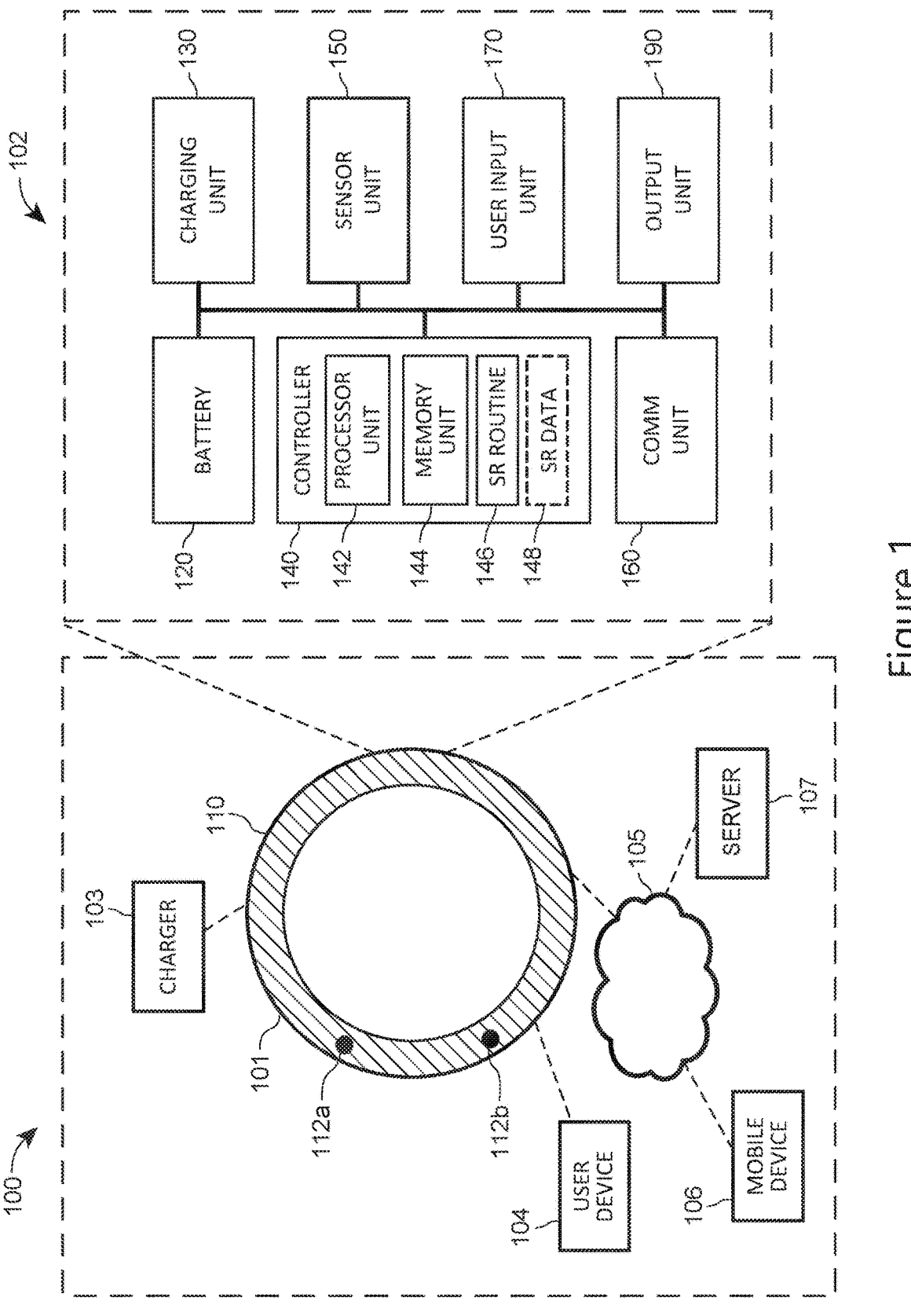
FIG. 1 illustrates a system comprising a smart ring and a block diagram of smart ring components according to some embodiments.
Figure 2:
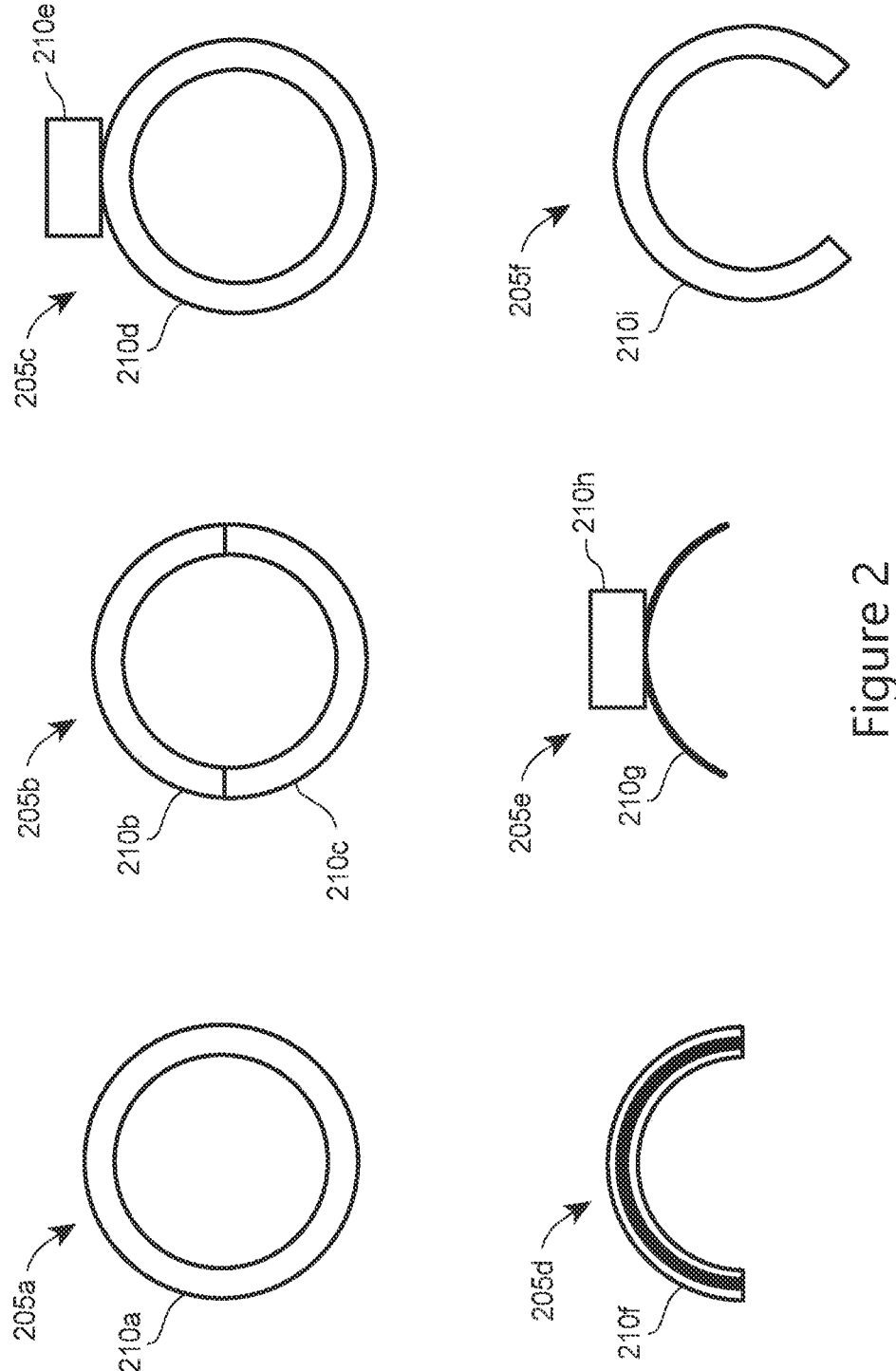
FIG. 2 illustrates a number of different form factor types of a smart ring according to some embodiments.
Figure 3:
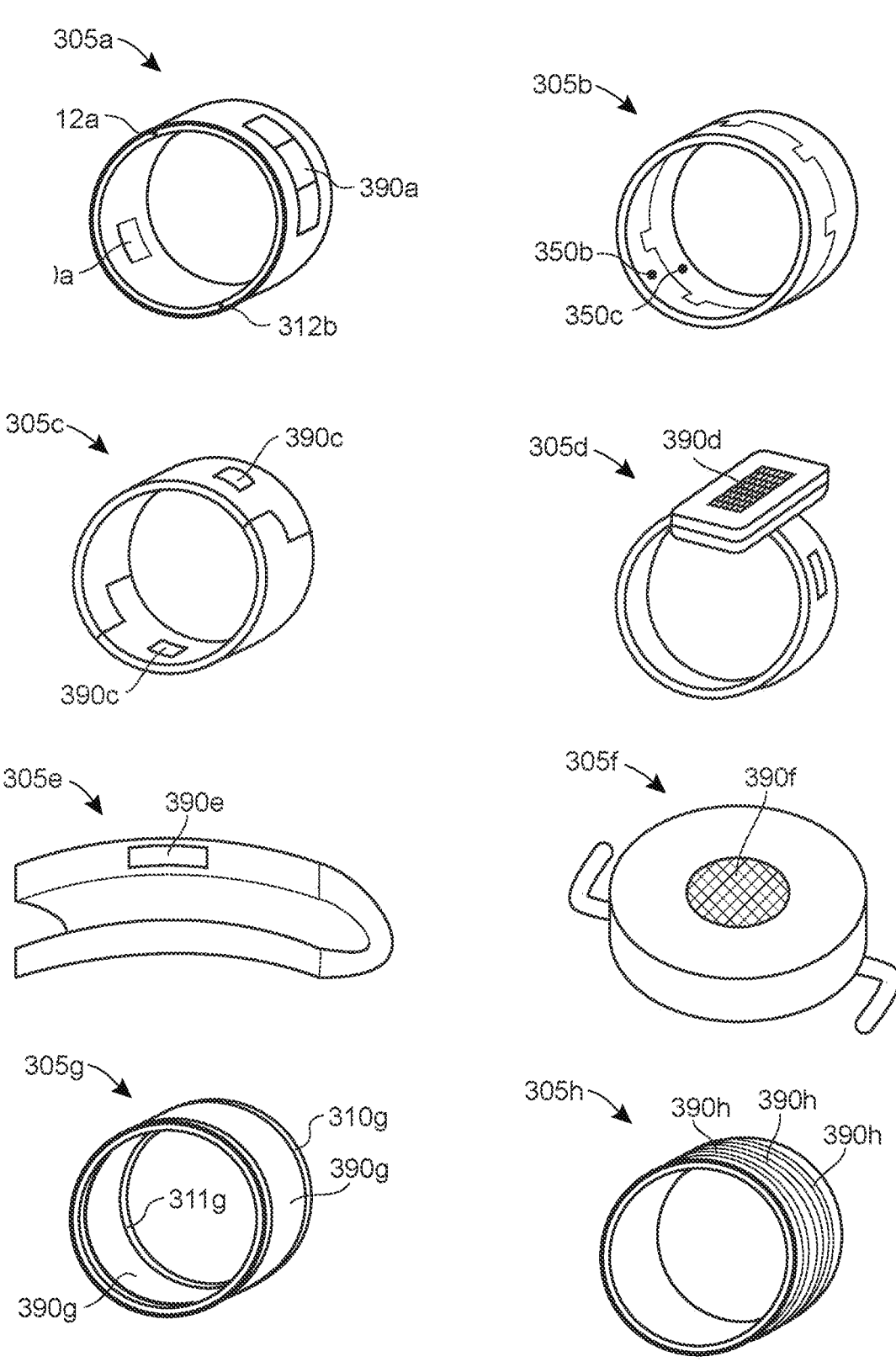
FIG. 3 illustrates examples of different smart ring form factors and configurations according to some embodiments.
Figure 4A:
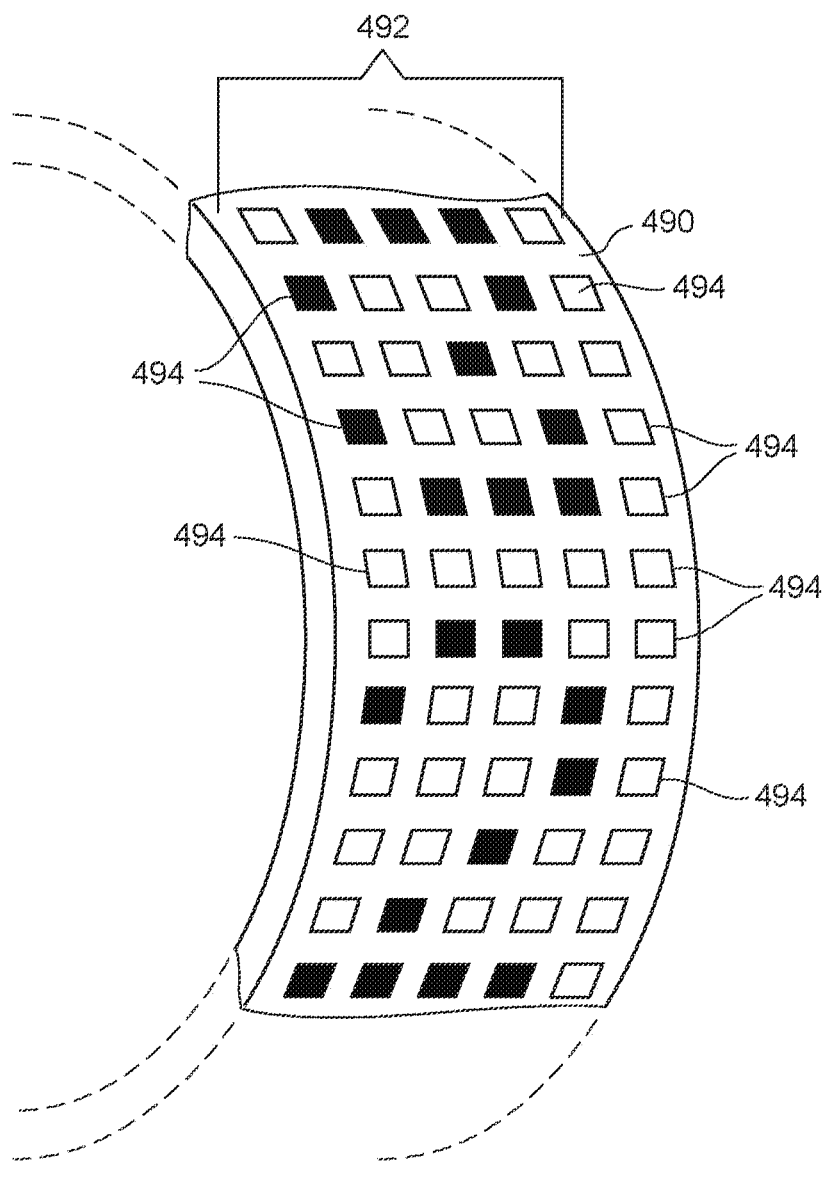
FIG. 4A is an illustration of an output device with an LED array for displaying characters and symbols according to some embodiments.
Figure 4B:
FIG. 4B and FIG. 4C illustrate the scrolling of a message across an LED array of an output device according to some embodiments.
Figure 4C:
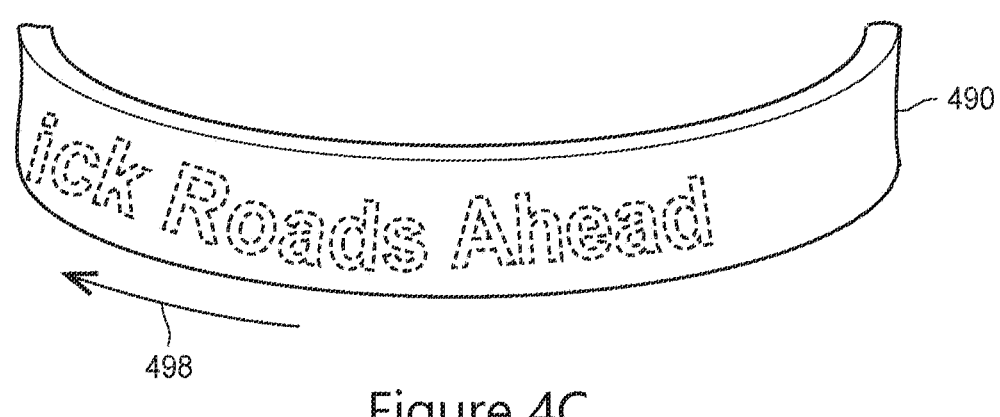
Figure 5:
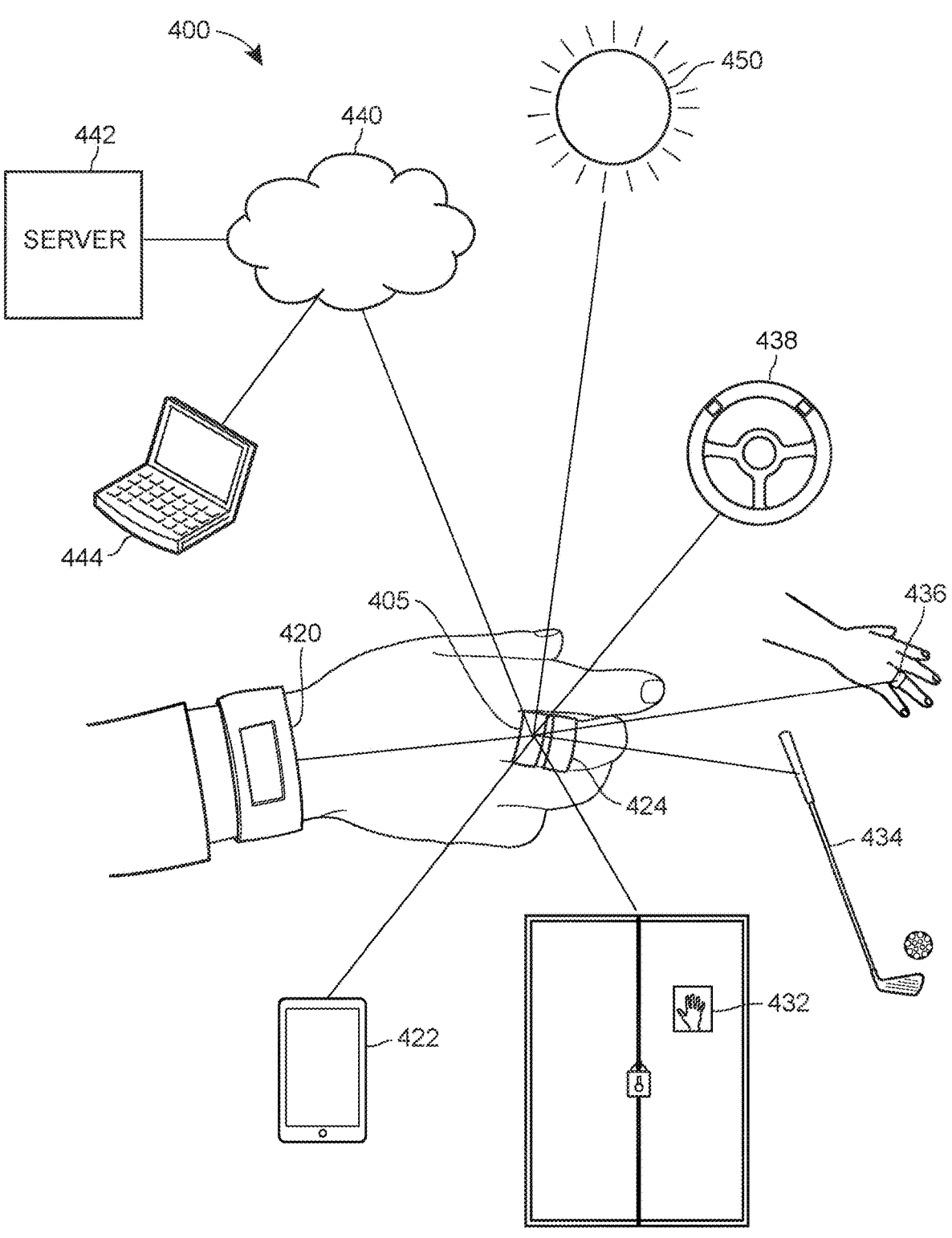
FIG. 5 illustrates an environment within which a smart ring may operate according to some embodiments.

Various techniques, systems, and methods are described below with reference to FIG. 1, FIG. 2, FIG. 3, FIG. 4, and FIG. 5. FIG. 1 and FIG. 5 illustrate example systems and system components that incorporate a smart ring. FIG. 2 and FIG. 3 depict various form factors and configurations of smart ring embodiments. FIG. 4A, FIG. 4B, and FIG. 4C depict smart ring devices with LED displays for displaying information.

Specifically, the following is described: (I) an example smart ring system 100 (shown in FIG. 1), configured to present information indicative of driving conditions to a driver of a vehicle, including a smart ring 101, a set of smart ring components 102, and one or more devices or systems in communication with the smart ring including a user device 104, a mobile device 106, and a server 107; (II) smart ring form factor types of the smart ring 101 (FIG. 2); (III) example surface element configurations of the smart ring form factor types of the smart ring 101 (FIG. 3); (IV) examples of smart ring configurations with LED displays as output devices (FIG. 3); (V) smart ring examples with LED arrays for displaying characters and symbols (FIG. 4A, FIG. 4B, and FIG. 4C); (VI) an example environment 400 in which smart ring 101 may operate (FIG. 5), including (1) server 442 and (2) other sample devices; (IX) additional considerations; and (X) general terms and phrases.

The "driving conditions" identified by the smart ring or communicated by the smart ring to a user of the smart ring may be: (i) biometrics of a user of the smart ring including, without limitation, pulse rate, blood flow, blood oxygen level, blood pressure, skin salinity level, temperature, weariness level, a cognoscente condition of the user, an inebriation condition of the user, or any other biological and biometric information; (ii) a state of a user such as erratic behavior of the user, sleepiness of the user, or a stress level of the user; (iii) detected vehicular statuses such as engine temperature, oil level, a needed oil change, coolant level, exhaust fume legal compliance, break pad health, low battery charge, flat tire, alternator failure, tire alignment/misalignment, transmission issue, power steering fluid level, brake fluid level, transmission fluid level, windshield wiper fluid level, etc.; (iv) vehicular operations such as a speed of a vehicle, an acceleration of a vehicle, a current altitude of the vehicle, a lane centering of the vehicle, a fuel efficiency of the vehicle, an autopilot function status of the vehicle (e.g., autopilot is activated/not-activated), an operational of autonomous driving function of the vehicle is deactivated, an autonomous driving function of the vehicle is activated, air bags are activated/de-activated, a seat belt is latched/unlatched, a temperature of the environment inside of the cabin of the vehicle, etc.; external factors or environmental factors such as current or predicated weather conditions (e.g., rain, snow, extreme heat, etc.), current external environmental conditions (e.g., wet/slick roads, fog levels, a visibility level, dangerous breathing air, external temperature, etc.), current conditions inside of the cab of the vehicle (e.g., the temperature, air quality, moisture level, etc.); information and statuses of nearby vehicles, identifications that a nearby driver is driving erratically; driving conditions during operation of a vehicle such as the congestion of drivers along a road or planned trip route, the current proximity of the vehicle to external objects outside of the vehicle (e.g., other vehicles, pedestrians, trees, etc.), or other factors associated with operation of a vehicle; or another element or factor that may have an influence or impact of the operation of a vehicle.

The "data" that is received by a processor of the smart ring (via a sensor or communication module of the smart ring) and analyzed by the processor to identify the one or more driving conditions may include: biometric data of a wearer of the smart ring (e.g., representing detect heart beats, perspiration, user movement, etc.), biometric data from a user associated device, data from sensors of the vehicle (e.g., speed data, direction data, laser or camera data representing captured information regarding environmental or road conditions), data from a central console of the vehicle, data from sensors of other vehicles, data from central consoles of other vehicles, data from user associated devices or drivers from other vehicles, data from a network, data associated with a driving history of a driver, data associated with a health history of a driver, data associated with behavior trends of a driver, or data indicative of any of the driving conditions described above.

I. An Example Smart Ring Environment

FIG. 1 illustrates a system 100 that may be utilized to display relevant information to a driver, thereby improving the driver's awareness of the state of the vehicle, environment, and even his or her own state and consequently improving the driver's safety profile and reducing his or her risk exposure while driving. The system 100 may obtain information indicative of driving conditions as described herein to display information indicative of the driving conditions to the driver of the vehicle.

The system 100 comprises (i) a smart ring 101 including a set of components 102 and (ii) one or more devices or systems that may be electrically, mechanically, or communicatively connected to the smart ring 101. Specifically, the system 100 may comprise any one or more of: a charger 103 for the smart ring 101, a user device 104, a network 105, a mobile device 106, or a server 107. The charger 103 may provide energy to the smart ring 101 by way of a direct electrical, a wireless, or an optical connection. The smart ring 101 may be in a direct communicative connection with the user device 104, the mobile device 106, or the server 107 by way of the network 105. Interactions between the smart ring 101 and other components of the system 100 are discussed in more detail in the context of FIG. 5.

The smart ring 101 may sense a variety of signals indicative of activities of a user wearing the ring 101, biometric signals, a physiological state of the user, or signals indicative of the user's environment. The smart ring 101 may analyze the sensed signals using built-in computing capabilities or in cooperation with other computing devices (e.g., user device 104, mobile device 106, server 107) and provide feedback to the user or about the user via the smart ring 101 or other devices (e.g., user device 104, mobile device 106, server 107). The smart ring 101 may process the sensed signals and provide visual outputs to the user of the smart ring 101 indicative of any of the sensed signals, as discussed further below. Additionally or alternatively, the smart ring 101 may provide the user with notifications sent by other devices, enable secure access to locations or information, or a variety of other applications pertaining to health, wellness, productivity, or entertainment.

The smart ring 101, which may be referred to herein as the ring 101, may comprise a variety of mechanical, electrical, optical, or any other suitable subsystems, devices, components, or parts disposed within, at, throughout, or in mechanical connection to a housing 110 (which may be ring shaped and generally configured to be worn on a finger). Additionally, a set of interface components 112a and 112b may be disposed at the housing, and, in particular, through the surface of the housing. The interface components 112a and 112b may provide a physical access (e.g., electrical, fluidic, mechanical, or optical) to the components disposed within the housing. The interface components 112a and 112b may exemplify surface elements disposed at the housing. As discussed below, some of the surface elements of the housing may also be parts of the smart ring components.

As shown in FIG. 1, the components 102 of the smart ring 101 may be distributed within, throughout, or on the housing 110. As discussed in the contexts of FIG. 2 and FIG. 3 below, the housing 110 may be configured in a variety of ways and include multiple parts. The smart ring components 102 may, for example, be distributed among the different parts of the housing 110, as described below, and may include surface elements of the housing 110. The housing 110 may include mechanical, electrical, optical, or any other suitable subsystems, devices, components, or parts disposed within or in mechanical connection to the housing 110, including a battery 120, a charging unit 130, a controller 140, a sensor system 150 comprising one or more sensors, a communications unit 160, a one or more user input devices 170, or a one or more output devices 190. Each of the components 120, 130, 140, 150, 160, 170, and/or 190 may include one or more associated circuits, as well as packaging elements. The components 120, 130, 140, 150, 160, 170, and/or 190 may be electrically or communicatively connected with each other (e.g., via one or more busses or links, power lines, etc.), and may cooperate to enable "smart" functionality described within this disclosure.

The battery 120 may supply energy or power to the controller 140, the sensors 150, the communications unit 160, the user input devices 170, or the output devices 190. In some scenarios or implementations, the battery 120 may supply energy or power to the charging unit 130. The charging unit 130 may supply energy or power to the battery 120. In some implementations, the charging unit 130 may supply (e.g., from the charger 103, or harvested from other sources) energy or power to the controller 140, the sensors 150, the communications unit 160, the user input devices 170, or the output devices 190. In a charging mode of operation of the smart ring 101, the average power supplied by the charging unit 130 to the battery 120 may exceed the average power supplied by the battery 120 to the charging unit 130, resulting in a net transfer of energy from the charging unit 130 to the battery 120. In a non-charging mode of operation, the charging unit 130 may, on average, draw energy from the battery 120.

The battery 120 may include one or more cells that convert chemical, thermal, nuclear or another suitable form of energy into electrical energy to power other components or subsystems 140, 150, 160, 170, and/or 190 of the smart ring 101. The battery 120 may include one or more alkaline, lithium, lithium-ion and or other suitable cells. The battery 120 may include two terminals that, in operation, maintain a substantially fixed voltage of 1.5, 3, 4.5, 6, 9, 12 V or any other suitable terminal voltage between them. When fully charged, the battery 120 may be capable of delivering to power-sinking components an amount of charge, referred to herein as "full charge," without recharging. The full charge of the battery may be 1, 2, 5, 10, 20, 50, 100, 200, 500, 1000, 2000, 5000 mAh or any other suitable charge that can be delivered to one or more power-consuming loads as electrical current.

The battery 120 may include a charge-storage device, such as, for example a capacitor or a super-capacitor. In some implementations discussed below, the battery 120 may be entirely composed of one or more capacitive or charge-storage elements. The charge storage device may be capable of delivering higher currents than the energy-conversion cells included in the battery 120. Furthermore, the charge storage device may maintain voltage available to the components or subsystems 130, 140, 150, 160, 170, and/or 190 when one or more cells of the battery 120 are removed to be subsequently replaced by other cells.

The charging unit 130 may be configured to replenish the charge supplied by the battery 120 to power-sinking components or subsystems (e.g., one or more of subsystems 130, 140, 150, 160, 170, and/or 190) or, more specifically, by their associated circuits. To replenish the battery charge, the charging unit 130 may convert one form of electrical energy into another form of electrical energy. More specifically, the charging unit 130 may convert alternating current (AC) to direct current (DC), may perform frequency conversions of current or voltage waveforms, or may convert energy stored in static electric fields or static magnetic fields into direct current. Additionally or alternatively, the charging unit 130 may harvest energy from radiating or evanescent electromagnetic fields (including optical radiation) and convert it into the charge stored in the battery 120. Furthermore, the charging unit 130 may convert non-electrical energy into electrical energy. For example, the charging unit 130 may harvest energy from motion, or from thermal gradients.

The controller 140 may include a processor unit 142 and a memory unit 144. The processor unit 142 may include one or more processors, such as a microprocessor (μP), a digital signal processor (DSP), a central processing unit (CPU), a graphical processing unit (GPU), a field-programmable gate array (FPGA), an application-specific integrated circuit (ASIC), or any other suitable electronic processing components. In embodiments, the controller may include a dedicated graphics-processing unit (GPU) for rendering images, animations, characters, symbols, or any visual outputs to be presented to the user of the smart ring 101. Additionally or alternatively, the processor unit 142 may include photonic processing components (e.g., cameras, optical sensors, waveguide, optical storage, optical switches, light emitting diodes (LEDs) laser diode (LDs), etc.).

The memory unit 144 may include one or more computer memory devices or components, such as one or more registers, RAM, ROM, EEPROM, or on-board flash memory. The memory unit 144 may use magnetic, optical, electronic, spintronic, or any other suitable storage technology. In some implementations, at least some of the functionality the memory unit 144 may be integrated in an ASIC or and FPGA. Furthermore, the memory unit 144 may be integrated into the same chip as the processor unit 142 and the chip, in some implementations, may be an ASIC or an FPGA.

The memory unit 144 may store a smart ring (SR) routine 146 with a set of instructions, that, when executed by the processor 142 may enable the operation and the functionality described in more detail below. Furthermore, the memory unit 144 may store smart ring (SR) data 148, which may include (i) input data used by one or more of the components 102 (e.g., by the controller when implementing the SR routine 146) or (ii) output data generated by one or more of the components 102 (e.g., the controller 140, the sensor unit 150, the communication unit 160, or the user input unit 170). In some implementations, other units, components, or devices may generate data (e.g., diagnostic data) for storing in the memory unit 144.

The processing unit 142 may draw power from the battery 120 (or directly from the charging unit 130) to read from the memory unit 144 and to execute instructions contained in the smart ring routine 146. Likewise, the memory unit 144 may draw power from the battery 120 (or directly from the charging unit 130) to maintain the stored data or to enable reading or writing data into the memory unit 144. The processor unit 142, the memory unit 144, or the controller 140 as a whole may be capable of operating in one or more low-power mode. One such low power mode may maintain the machine state of the controller 140 when less than a threshold power is available from the battery 120 or during a charging operation in which one or more battery cells are exchanged.

The controller 140 may receive and process data from the sensors 150, the communications unit 160, or the user input devices 170. The controller 140 may perform computations to generate new data, signals, or information. The controller 140 may send data from the memory unit 144 or the generated data to the communication unit 160 or the output devices 190. The electrical signals or waveforms generated by the controller 140 may include digital or analog signals or waveforms. The controller 140 may include electrical or electronic circuits for detecting, transforming (e.g., linearly or non-linearly filtering, amplifying, attenuating), or converting (e.g., digital to analog, analog to digital, rectifying, changing frequency) of analog or digital electrical signals or waveforms.

The sensor unit 150 may include one or more sensors disposed within or throughout the housing 110 of the ring 101. Each of the one or more sensors may transduce one or more of: light, sound, acceleration, translational or rotational movement, strain, temperature, chemical composition, surface conductivity, pressure, or other suitable signals into electrical or electronic sensors or signals. A sensor may be acoustic, photonic, micro-electro-mechanical systems (MEMS) sensors, chemical, micro-fluidic (e.g., flow sensor), or any other suitable type of sensor. The sensor unit 150 may include, for example, an inertial motion unit (IMU) for detecting orientation and movement of the ring 101.

The communication unit 160 may facilitate wired or wireless communication between the ring 101 and one or more other devices. The communication unit 160 may include, for example, a network adaptor to connect to a computer network, and, via the network, to network-connected devices. The computer network may be the Internet or another type of suitable network (e.g., a personal area network (PAN), a local area network (LAN), a metropolitan area network (MAN), a wide area network (WAN), a mobile, a wired or wireless network, a private network, a virtual private network, etc.). The communication unit 160 may use one or more wireless protocols, standards, or technologies for communication, such as Wi-Fi, near field communication (NFC), Bluetooth, or Bluetooth low energy (BLE). Additionally or alternatively, the communication unit 160 may enable free-space optical or acoustic links. In some implementations, the communication unit 160 may include one or more ports for a wired communication connections. The wired connections used by the wireless communication module 160 may include electrical or optical connections (e.g., fiber-optic, twisted-pair, coaxial cable).

User input unit 170 may collect information from a person wearing the ring 101 or another user, capable of interacting with the ring 101. In some implementations, one or more of the sensors in the sensor unit 150 may act as user input devices within the user input unit 170. User input devices may transduce tactile, acoustic, video, gesture, or any other suitable user input into digital or analog electrical signal, and send these electrical signals to the controller 140.

The output unit 190 may include one or more devices to output information to a user of the ring 101. The one or more output devices may include acoustic devices (e.g., speaker, ultrasonic); haptic (thermal, electrical) devices; electronic displays for optical output, such as an organic light emitting device (OLED) display, a laser unit, a high-power light-emitting device (LED), etc.; or any other suitable types of devices. For example, the output unit 190 may include a projector that projects an image onto a suitable surface. In some implementations, the sensor unit 150, the user input unit 170, and the output unit 190 may cooperate to create a user interface with capabilities (e.g., a keyboard) of much larger computer systems, as described in more detail below.

The components 120, 130, 140, 150, 160, 170, and/or 190 may be interconnected by a bus 195, which may be implemented using one or more circuit board traces, wires, or other electrical, optoelectronic, or optical connections. The bus 195 may be a collection of electrical power or communicative interconnections. The communicative interconnections may be configured to carry signals that conform to any one or more of a variety of protocols, such as I2C, SPI, or other logic to enable cooperation of the various components.

II. Example Form Factor Types for a Smart Ring

FIG. 2 includes block diagrams of a number of different example form factor types or configurations 205a, 205b, 205c, 205d, 205e, and/or 205f of a smart ring (e.g., the smart ring 101) that may be utilized to display information indicative of driving conditions to a driver, thereby improving the driver's awareness of the state of the vehicle, environment, and even his or her own state and consequently improving the driver's safety profile and reducing his or her risk exposure while driving. The system configurations 205a, 205b, 205c, 205d, 205e, and/or 205f may obtain information indicative of the driving conditions via sensors disposed on/or within the configurations, or from communicating with external devices.

The configurations 205a, 205b, 205c, 205d, 205e, and/or 205f (which may also be referred to as the smart rings 205a, 205b, 205c, 205d, 205e, and/or 205f) may each represent an implementation of the smart ring 101, and each may include any one or more of the components 102 (or components similar to the components 102). In some embodiments, one or more of the components 102 may not be included in the configurations 205a, 205b, 205c, 205d, 205e, and/or 205f. The configurations 205a, 205b, 205c, 205d, 205e, and/or

205f include housings 210a-f, which may be similar to the housing 110 shown in FIG. 1.

The configuration 205a may be referred to as a band-only configuration comprising a housing 210a. In the configuration 205b, a band may include two or more removably connected parts, such as the housing parts 210b and 210c. The two housing parts 210b and 210c may each house at least some of the components 102, distributed between the housing parks 210b and 210c in any suitable manner. The configuration 205c may be referred to as a band-and-platform configuration comprising (i) a housing component 210d and (ii) a housing component 210e (sometimes called the "platform 210e"), which may be in a fixed or removable mechanical connection with the housing 210d. The platform 210e may function as a mount for a "jewel" or for any other suitable attachment. The housing component 210d and the platform 210e may each house at least one or more of the components 102 (or similar components).

In some instances, the term "smart ring" may refer to a partial ring that houses one or more components (e.g., components 102) that enable the smart ring functionality described herein. The configurations 205d and 205e may be characterized as "partial" smart rings, and may be configured for attachment to a second ring. The second ring may be a conventional ring without smart functionality, or may be second smart ring, wherein some smart functionality of the first or second rings may be enhanced by the attachment.

The configuration 205d, for example, may include a housing 210f with a groove to enable clipping onto a conventional ring. The grooved clip-on housing 210f may house the smart ring components described above. The configuration 205e may clip onto a conventional ring using a substantially flat clip 210g part of the housing and contain the smart ring components in a platform 210h part of the housing.

The configuration 205f, on the other hand, may be configured to be capable of being mounted onto a finger of a user without additional support (e.g., another ring). To that end, the housing 210i of the configuration 205f may be substantially of a partial annular shape subtending between 180 and 360 degrees of a full circumference. When implemented as a partial annular shape, the housing 210i may be more adaptable to fingers of different sizes that a fully annular band (360 degrees), and may be elastic. A restorative force produced by a deformation of the housing 210i may ensure a suitable physical contact with the finger. Additional suitable combinations of configurations (not illustrated) may combine at least some of the housing features discussed above.

III. Example Surface Elements of a Smart Ring

FIG. 3 includes perspective views of example configurations 305a, 305b, 305c, 305d, 305e, 305f, 305g, and/or 305h of a smart ring (e.g., the smart ring 101) in which a number of surface elements are included. The surface elements may include sensors for detecting information indicative of driving conditions, or receive information indicative of driving conditions from external devices. The surface elements may also include output elements for displaying information indicative of the driving conditions to a driver.

The configuration 305a is an example band configuration 305a of a smart ring (e.g., smart ring 101). Some of the surface elements of the housing may include interfaces 312a, 312b that may be electrically connected to, for example, the charging unit 130 or the communications unit 160. On the outside of the configuration 305a, the interfaces 312a, 312b may be electrically or optically connected with a charger to transfer energy from the charger to a battery (e.g., the battery 120), or with another device to transfer data to or from the ring 305a. The outer surface of the configuration 305a may include a display 390a, while the inner surface may include a biometric sensor 350a.

Configurations 305b and 305c are examples of configurations of a smart ring with multiple housing parts (e.g., the configuration 205b in FIG. 2). Two (or more) parts may be separate axially (the configuration 305b), azimuthally (the configuration 305c), or radially (nested rings, not shown). The parts may be connected mechanically, electrically, or optically via, for example, interfaces analogous to the interfaces 312a, 312b in configuration 305a. Each part of a smart ring housing may have one or more surface elements, such as, for example, sensors 350b, 350c or output elements 390b, 290c. The latter may be LEDs (e.g., output element 390b) or haptic feedback devices (e.g., output element 390c), among other suitable sensor or output devices. Additionally or alternatively, at least some of the surface elements (e.g., microphones, touch sensors) may belong to the user input unit 170.

The configuration 305d may be an example of a band and platform configuration (e.g., the configuration 205c), while the configurations 305e and 305f may be examples of the partial ring configurations 205d and 205e, respectively. Output devices 390d, 390e, and/or 390f on the corresponding configurations 305d, 305e, and/or 305f may be LCD displays, OLED displays, e-ink displays, one or more LED pixels, speakers, or any other suitable output devices that may be a part of a suite of outputs represented by an output unit (e.g., the output unit 190).

The configuration 305g is an example of a band with a one or more output devices 390g disposed on an outer surface 310g and an inner surface 311g of the ring band. In embodiments, the output devices 390g may be disposed on first and second side surfaces 308g and 309g of the ring band. Alternatively, the output devices 390g may be disposed within the inner and outer surfaces 310g and 311g, or the first and second side surfaces 308g and 309g, of the ring band configured to be viewed by a user of the smart ring configuration 305g. For example, in embodiments the outer and inner surfaces 310g and 311g or first and second side surfaces 308g and 309g may be transparent. The output devices 390g may be viewable from the entirety of the outer surface 310g, the entirety of the inner surface 311g, the entirety of the first side surface 308g, or the entirety of the second side surface 309g respectively. In embodiments, the output devices 390g may be disposed on or viewable from only a portion of each of the surfaces 310g and 311g. Additionally, sensors may be operatively coupled to the configuration 305g (e.g., elements and sensors of the user input unit 170 of FIG. 1) to detect a user input to determine where on the output devices 390g information should be displayed. For example, a user may press a finger or stylus on the outer surface 310g to indicate the information should be displayed on the outer surface 310g. Alternatively, the ring may be removed from a finger, or digit, of a user, or wearer, of the smart ring, and the user may press a finger or stylus on the inner surface 311g to indicate that information should be displayed on the inner surface 311g. The output device 390g on the inner surface 311g may then display the information for a user to view the information while the smart ring is not worn by the user of the smart ring device having the configuration 305g. A user of the configuration 305g may prefer information to be selectively viewable from the outer or inner surfaces 310g and 311g, or the first and second side surfaces 308g and 309g, depending on the type of information, potential content of the information, a current environment where the user is viewing the information, or depending on privacy concerns among other considerations. Alternatively, a user may press on a surface to indicate where the information should not be displayed.

Elements of the user input unit 170 may be coupled to the output devices 390g and a user may press on a portion of the output devices 390g to indicate that information should be presented from the portion of the output devices 390g that was pressed. Additionally, a user may indicate where the output devices 390g should display information dependent on different types of user inputs (e.g., audio input, twisting of the ring, removal of the smart ring from a finger or digit, placement of the ring on a finger or digit, a physical orientation of the ring, a change in orientation of the ring, etc.). In embodiments, the smart ring configurations 305a, 305b, 305c, 305d, 305e, 305f, and/or 305g may include an inertial motion unit (IMU) for detecting the orientation and/or the movement of the ring having one of the configurations 305a, 305b, 305c, 305d, 305e, 305f, and/or 305g. The orientation or a change in the orientation of the smart ring configuration 305a, 305b, 305c, 305d, 305e, 305f, and/or 305g may be analyzed by a processor of the smart ring configurations 305a, 305b, 305c, 305d, 305e, 305f, and/or 305g to determine which of the output devices 390a, 390b, 390c, 390d, 390e, 390f, and/or 390g to display the information, or to determine a portion, or portions, of the output devices 390a, 390b, 390c, 390d, 390e, 390f, and/or 390g that are to display information. In embodiments, the output devices 390a, 390b, 390c, 390d, 390e, 390f, and/or 390g may display an indication of a message or information that is ready to be presented to a user. The user may then provide the user input to the smart ring, based at least in part upon the indication, to indicate which output device 390g should display the information, and/or what portion of the output device should display the information. Enabling the user to indicate a portion of the display for displaying information may be useful in a number of contexts. For example, this feature enables a user to selectively view information at a time and portion (e.g., on the inside surface of the band when the band is removed) when he or she alone can view the information, thus providing the user with privacy he or she might not otherwise have. Further, in some embodiments, the band may have a display that occupies a significant portion of the outer band. In such embodiments, portions of the display may not be viewable by the user (e.g., because those portions may be viewable only from the palm-side of the hand). Thus, in such embodiments it may be advantageous to enable the user to indicate a desired portion for display (e.g., a portion of the display viewable from the back-side of the hand).

The configuration 305h may be an example of a band with a one or more output devices 390h that are multiple strips that wrap around the band. In embodiments, the output devices 390h may be optical waveguides that are coupled to LEDs, or optical sources, to guide light from the LEDs or optical sources. The LEDs may change colors and the waveguides may guide the colored light around the ring emitting the light from the waveguides to communicate information to a user. For example, the waveguides may be side-emitting optical waveguides designed to emit light from the sides of the waveguides for viewing by a user of the configuration 305h. In embodiments, the waveguides may be edge emitting optical waveguides configured to have the edges of the waveguide emit light from the output devices 390h. The output devices 390h may each be coupled to individual respective LEDs, or LED arrays, so that each of the output devices can present different colors indicative of different information. For example, one of the output devices 305*h* may change color to indicate the status' or operations of the smart ring (e.g., battery life, downloading information, upload information, communication link status, etc.), and another of the output devices 305*h* may change color to convey information pertaining to biometrics of a user of the smart ring (e.g., pulse rate, blood-oxygen level, blood flow information, temperature, etc.), while yet another of the output devices 305*h* may be configured to change color to convey information indicative of status of a vehicle component, or vehicle operation (e.g., low fuel, temperature of an engine, tire air pressure, speed, etc.). While illustrated as three strips, the output devices 305*h* wrapping the band may be 1 strip, 2 strips, 4 strips, 5 strips, 6 strips, or greater, depending on the spatial dimensions of the strips and the band.

IV. Example Smart Ring LED Displays

Staying with FIG. 3, the output devices 390*a*, 390*b*, 390*c*, 390*d*, 390*e*, 390*f*, 390*g*, and/or 390*h* may be LED displays each including one or more LEDs for displaying information indicative of one or more driving conditions identified by the smart ring.

The output devices 390*a*, 390*b*, 390*c*, 390*d*, 390*e*, 390*f*, 390*g*, and/or 390*h* may change color to convey information indicative of driving conditions to a user of a smart ring. For example, the output devices 390*a*, 390*b*, 390*c*, 390*d*, 390*e*, 390*f*, 390*g*, and/or 390*h* may change to the color red to indicate a low battery charge level, or other malfunction, of the smart ring. Additionally, LEDs of the output devices 390*a*, 390*b*, 390*c*, 390*d*, 390*e*, 390*f*, 390*g*, and/or 390*h* may be configured to emit any color (e.g., green blue, red, violet, yellow, orange, etc.) to indicate any type of operation or status of the smart ring. For example, the output devices 390*a*, 390*b*, 390*c*, 390*d*, 390*e*, 390*f*, 390*g*, and/or 390*h* may emit colors based at least in part upon the battery level of the smart ring, an incoming communication being received by the smart ring, an outgoing communication being sent from the smart ring, an active or inactive communicative link between the smart ring and an external device, etc.

In embodiments, the output devices 390*a*, 390*b*, 390*c*, 390*d*, 390*e*, 390*f*, 390*g*, and/or 390*h* may change color dependent on detected biometrics of a user of the smart ring. For example, the smart ring may detect the pulse of a user of the smart ring, and the output devices 390*a*, 390*b*, 390*c*, 390*d*, 390*e*, 390*f*, 390*g*, and/or 390*h* may present the color red if the detected pulse rate is above a maximum pulse rate threshold or below a minimum pulse rate threshold, and the output devices 390*a*, 390*b*, 390*c*, 390*d*, 390*e*, 390*f*, 390*g*, and/or 390*h* may present the color green if the detected pulse rate is between the maximum and minimum pulse rate thresholds. LEDs and LED arrays of the output devices 390*a*, 390*b*, 390*c*, 390*d*, 390*e*, 390*f*, 390*g*, and/or 390*h* may change to any color to indicate information indicative of a pulse rate, blood flow, blood oxygen level, blood pressure, skin salinity level, temperature, weariness level, a cognoscente condition of the user, an inebriation condition of the user, or any other biological and biometric information to a user of the smart ring. Additionally, the ring may display indications of a state of a user such as erratic behavior of the sure, sleepiness of the user, stress level of the user, etc.

In embodiments, the output devices 390*a*, 390*b*, 390*c*, 390*d*, 390*e*, 390*f*, 390*g*, and/or 390*h* may display a color dependent on detected vehicular statuses. For example, the smart ring may communicate with sensors of a vehicle, with a communication module of the vehicle, or with another device or network to obtain current statuses of the vehicle and parts of the vehicle. For example, the output devices 390*a*, 390*b*, 390*c*, 390*d*, 390*e*, 390*f*, 390*g*, and/or 390*h* may display the color red to indicate that the gas in the tank of a vehicle is below a minimum threshold. The output devices may similarly display the color red, or another color, to indicate that the heat of the engine of the vehicle is too high or a tire of the vehicle has an air pressure below a threshold. Additionally, the output devices may display color to present information to the user indicative of an oil level, needed oil change, coolant level, exhaust fume legal compliance, break pad health, low battery charge, flat tire, alternator failure, tire alignment/misalignment, transmission issue, power steering fluid level, brake fluid level, transmission fluid level, windshield wiper fluid level, etc.

In embodiments, the output devices 390*a*, 390*b*, 390*c*, 390*d*, 390*e*, 390*f*, 390*g*, and/or 390*h* may display a color dependent on vehicular operations. For example, the smart ring may communicate with sensors of the vehicle, with a communication module of the vehicle, or with another device or network to obtain a current speed of the vehicle. The output devices 390*a*, 390*b*, 390*c*, 390*d*, 390*e*, 390*f*, 390*g*, and/or 390*h* may present the color red if the speed is above a maximum speed threshold or below a minimum speed threshold, and the output devices 390*a*, 390*b*, 390*c*, 390*d*, 390*e*, 390*f*, 390*g*, and/or 390*h* may present the color green if the detected speed is between the maximum and minimum speed thresholds. In embodiments, the output devices 390*a*, 390*b*, 390*c*, 390*d*, 390*e*, 390*f*, 390*g*, and/or 390*h* may change color to present to a user, information indicative of a speed of a vehicle, an acceleration of a vehicle, a current altitude of the vehicle, the lane centering of the vehicle, a fuel efficiency of the vehicle, an autopilot function status of the vehicle (e.g., autopilot is activated/not-activated), an autonomous driving function of the vehicle is operational, an autonomous driving function of the vehicle is activated, air bags are activated/de-activated, a seat belt is latched/unlatched, a temperature of the environment inside of the cabin of the vehicle, etc.

In embodiments, the output devices 390*a*, 390*b*, 390*c*, 390*d*, 390*e*, 390*f*, 390*g*, and/or 390*h* may display a color dependent on external factors or environmental factors in, and around, the vehicle. For example, the smart ring may communicate with sensors of the vehicle, with a communication module of the vehicle, with communication modules of other nearby vehicles, with a mobile device of the user of the smart ring, or with another device or network to obtain information and statuses of nearby vehicles. For example, it may be communicated to the smart ring that a nearby driver is driving erratically, and the smart ring may display the color red to indicate that the driver should be cautious. Additionally, the output devices may display signals and information indicative of current or predicated weather conditions (e.g., rain, snow, extreme heat, etc.), current external environmental conditions (e.g., wet/slick roads, fog levels, a visibility level, dangerous breathing air, external temperature, etc.), current conditions inside of the cab of the vehicle (e.g., the temperature, air quality, moisture level, etc.).

In embodiments, the output devices 390*a*, 390*b*, 390*c*, 390*d*, 390*e*, 390*f*, 390*g*, and/or 390*h* may output visual signals to indicate many driving conditions during operation of a vehicle such as the congestion of drivers along a road or planned trip route, the current proximity of the vehicle to external objects outside of the vehicle (e.g., other vehicles, pedestrians, trees, etc.), or other factors associated with operation of a vehicle.

The output devices 390*a*, 390*b*, 390*c*, 390*d*, 390*e*, 390*f*, 390*g*, and/or 390*h* may indicate to a user of a smart ring, any number of driving conditions as described above. Driving conditions may be considered to be any element or factor that may have an influence or impact on the operation of a vehicle. For example, the weariness of an operator of the vehicle may be considered to be a driving condition, as well as the visibility of a road due to a rainstorm. The driving conditions may include one or more of the examples above including, without limitation, any operation of a vehicle, status of a vehicle or part of a vehicle, biometric of a user of the smart ring, operation of the smart ring, statuses of the smart ring, external environmental factors, and external driving factors. Additionally, it is envisioned, that the user of the smart ring may be a driver of a vehicle and the biometric information may be used to determine the sleepiness of the driver, inebriation condition of the driver, or otherwise, cognoscente condition of the driver.

While described above as "changing" and "changing colors", the output devices 390*a*, 390*b*, 390*c*, 390*d*, 390*e*, 390*f*, 390*g*, and/or 390*h* may provide other visual signals or outputs indicative of driving conditions. For example, the output devices 390*a*, 390*b*, 390*c*, 390*d*, 390*e*, 390*f*, 390*g*, and/or 390*h* may each be one or more white, or monochromatic LEDs and information may be portrayed to a user through flashes or pulses of the LEDs, a degree of brightness of the LEDs, or a sequential illumination of multiple LEDs (e.g., a set of ten LEDs that sequentially turn off as the fuel in a fuel tank decreases, therefore indicating fuel level). The output devices 390*a*, 390*b*, 390*c*, 390*d*, 390*e*, 390*f*, 390*g*, and/or 390*h*, may include one or more LED arrays for displaying characters or symbols, as described in simultaneous reference to FIG. 3, FIG. 4A, FIG. 4B, and FIG. 4C.

V. An Example Smart Ring LED Array for Displaying Characters and Symbols

FIG. 4A, FIG. 4B, and FIG. 4C are example illustrations of an output device 490 having an LED array 492 for displaying characters and symbols indicative of driving conditions identified by a smart ring device. The output device may be any of the output devices 390*a*, 390*b*, 390*c*, 390*d*, 390*e*, 390*f*, 390*g*, and/or 390*h* of FIG. 3. The LED array 492 may illuminate LED elements 494 of the LED array 492 to display characters, symbols, words, or sentences, to a user of a smart ring device. The output device 490 may cause the LED array 492 to display a caution message that reads "Caution: Slick Roads Ahead." The message may be too long to display at one time on the output device 490 or from one point of view of the output device 490. The output device 490 may then display characters, symbols, words, and/or sentences sequentially in frames, for example displaying the word "Caution" for a few seconds, and then displaying a new frame with the words "Slick Roads Ahead." Displaying messages in frames allows for the output device 490 to display longer messages, but may not be suitable for smooth reading of entire sentences or text messages. Therefore, as illustrated in FIG. 4B and FIG. 4C, the output device 490 may cause the LED array 492 to illuminate LED elements 494 in a manner that the message is scrolled across the output device 490 in the direction 498 from right to left across the output device 490. The LED array 492 may activate the LED elements 494 to display and/or scroll any characters, symbols, sentences, or messages indicative of one or more driving conditions as described above.

Additionally, the output device 490 may display a symbol or series of symbols, such as a happy face, thumbs up, check mark, or other symbol that may be indicative of a driving condition. For example, a smart ring device may attempt to establish a communication link with a mobile device of the user of the smart ring device, or with a communications module of a vehicle being driven by the user of the smart ring device. The output device 490 may cause the LED elements 494 to display a check mark to indicate that the communication link has been successfully established.

In embodiments, the output unit 190 of FIG. 1, the output devices 390*a*, 390*b*, 390*c*, 390*d*, 390*e*, 390*f*, 390*g*, and/or 390*h*, and/or the output device 490, may include LEDs, and may be configured to illuminate the LEDs in specific patterns, generating an optical signal, to transmit information from a smart ring to another device or system. For example, the LEDs may generate optical pulses that transmit bits of information to an optical sensor to identify a user of the smart ring. One specific example includes communication, via the optical signal, the identification of a wearer of the smart ring to a smart lock or electronic lock of a vehicle. The optical signal received by the electronic lock may unlock the door depending on a confirmed identification of the wearer of the smart ring being an approved driver of the vehicle. Another example includes identifying the wearer of the smart ring to provide permissions to the wearer to operate a vehicle, to obtain statuses of the vehicle parts (e.g., engine performance information, coolant levels, etc.), to obtain a list or timestamped list of previous drivers of the vehicle, to obtain a history of maintenances performed on a vehicle, etc. Permissions may include providing access to an account associated with the wearer of the ring to transmit data and information from the smart ring device to a device (e.g., cellular device, network, laptop, etc.) accessing the account associated with the wearer of the smart ring, or to transmit data and information from a device accessing the account associated with the wearer of the smart ring to the smart ring device. The optical signal may be used to identify a user for logging into devices and computers, determining permissions to enter a room, permissions to open a cabinet or closet, identification and permissions at a medical facility, identification and permissions at an educational institution, clocking into/out of a work place, and identification for operation of a vehicle, among other identification purposes. The output unit 190 and output devices 390*a*, 390*b*, 390*c*, 390*d*, 390*e*, 390*f*, 390*g*, and/or 390*h*, and 490 may be configured to provide the optical signal to an optical fiber, optical waveguide, photodiode, avalanche photodiode, charge-coupled device, photoresistor, photomultiplier, imaging camera, or other optical sensor. Additionally, the optical signal may include one or more signal modulations including, but not limited to, on-off keying, amplitude shift keying, frequency shift key, binary phase shift keying, phase modulations, amplitude modulation, spatial modulations, polarization modulation, or a quadrature amplitude modulation.

It should be appreciated that a variety of suitable surface elements may be disposed at the illustrated configurations 305*a*, 305*b*, 305*c*, 305*d*, 305*e*, and/or 305*f* at largely interchangeable locations. For example, the output elements 390*d*, 390*e*, and/or 390*f* may be replaced with sensors (e.g., UV sensor, ambient light or noise sensors, etc.), user input devices (e.g., buttons, microphones, etc.), interfaces (e.g., including patch antennas or optoelectronic components communicatively connected to communications units), or other suitable surface elements.

VI. Example Devices with which a Smart Ring May Interact

FIG. 5 illustrates an example environment 400 within which a smart ring 405 may be configured to operate. Elements of the environment 400 may obtain information indicative of driving conditions, communicate them to the smart ring 405, and the smart ring 405 may display information indicative of the driving conditions via output elements of the smart ring (e.g., an LED, or LED array). In an embodiment, the smart ring 405 may be the smart ring 101. In some embodiments, the smart ring 405 may be any suitable smart ring capable of providing at least some of the functionality described herein. Depending on the embodiment, the smart ring 405 may be configured in a manner similar or equivalent to any of the configurations 205a, 205b, 205c, 205d, 205e, and/or 205f or configurations 305a, 305b, 305c, 305d, 305e, and/or 305f shown in FIG. 2 and FIG. 3.

The smart ring 405 may interact (e.g., by sensing, sending data, receiving data, receiving energy) with a variety of devices, such as bracelet 420 or another suitable wearable device, a mobile device 422 (e.g., a smart phone, a tablet, etc.) that may be, for example, the user device 104, another ring 424 (e.g., another smart ring, a charger for the smart ring 405, etc.), a secure access panel 432, a golf club 434 (or another recreational accessory), a smart ring 436 worn by another user, or a steering wheel 438 (or another vehicle interface). Additionally or alternatively, the smart ring 405 may be communicatively connected to a network 440 (e.g., WiFi, 5G cellular), and by way of the network 440 (e.g., network 105 in FIG. 1) to a server 442 (e.g., server 107 in FIG. 1) or a personal computer 444 (e.g., mobile device 106). Additionally or alternatively, the ring 405 may be configured to sense or harvest energy from natural environment, such as the sun 450.

The ring 405 may exchange data with other devices by communicatively connecting to the other devices using, for example, the communication unit 160. The communicative connection to other device may be initiated by the ring 405 in response to user input via the user input unit 170, in response to detecting trigger conditions using the sensor unit 150, or may be initiated by the other devices. The communicative connection may be wireless, wired electrical connection, or optical. In some implementation, establishing a communicative link may include establishing a mechanical connection. The ring 405 may display or otherwise convey to a user of the ring 405 information or data received from any devices communicatively coupled to the ring 405, and more specifically data indicative of one or more driving conditions as described herein.

The ring 405 may connect to other devices (e.g., a device with the charger 103 built in) to charge the battery 120. The connection to other devices for charging may enable the ring 405 to be recharged without the need for removing the ring 405 from the finger. For example, the bracelet 420 may include an energy source that may transfer the energy from the energy source to battery 120 of the ring 405 via the charging unit 430. To that end, an electrical (or optical) cable may extend from the bracelet 420 to an interface (e.g., interfaces 112a, 112b, 312a, 312b) disposed at the housing (e.g., housings 110, 210a, 210b, 210c, 210d, 210e, 210f, 210g, 210h, 210i) of the ring 405. The mobile device 422, the ring 424, the golf club 434, the steering wheel 438 may also include energy source configured as chargers (e.g., the charger 103) for the ring 405. The chargers for may transfer energy to the ring 405 via a wired or wireless (e.g., inductive coupling) connection with the charging unit 130 of the ring 405.

VI. Examples of Other Considerations

When implemented in software, any of the applications, services, and engines described herein may be stored in any tangible, non-transitory computer readable memory such as on a magnetic disk, a laser disk, solid state memory device, molecular memory storage device, or other storage medium, in a RAM or ROM of a computer or processor, etc. Although the example systems disclosed herein are disclosed as including, among other components, software or firmware executed on hardware, it should be noted that such systems are merely illustrative and should not be considered as limiting. For example, it is contemplated that any or all of these hardware, software, and firmware components could be embodied exclusively in hardware, exclusively in software, or in any combination of hardware and software. Accordingly, while the example systems described herein are described as being implemented in software executed on a processor of one or more computer devices, persons of ordinary skill in the art will readily appreciate that the examples provided are not the only way to implement such systems.

The described functions may be implemented, in whole or in part, by the devices, circuits, or routines of the system 100 shown in FIG. 1. Each of the described methods may be embodied by a set of circuits that are permanently or semi-permanently configured (e.g., an ASIC or FPGA) to perform logical functions of the respective method or that are at least temporarily configured (e.g., one or more processors and a set instructions or routines, representing the logical functions, saved to a memory) to perform the logical functions of the respective method.

While the present disclosure has been described with reference to specific examples, which are intended to be illustrative only and not to be limiting of the present disclosure, it will be apparent to those of ordinary skill in the art that changes, additions or deletions may be made to the disclosed embodiments without departing from the spirit and scope of the present disclosure.

Throughout this specification, plural instances may implement components, operations, or structures described as a single instance. Although individual operations of one or more methods are illustrated and described as separate operations, one or more of the individual operations may be performed concurrently in certain embodiments.

As used herein, any reference to "one embodiment" or "an embodiment" means that a particular element, feature, structure, or characteristic described in connection with the embodiment is included in at least one embodiment. The appearances of the phrase "in one embodiment" in various places in the specification may not all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements may not be limited to only those elements but may include other elements not expressly listed or inherent to such process, method, article, or apparatus. Further, unless expressly stated to the contrary, "or" refers to an inclusive "or" and not to an exclusive "or." For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. Generally speaking, when a system or technique is described as including "a" part or "a" step, the system or technique should be read to include one or at least one part or step. Said another way, for example, a system described as including a blue widget may include multiple blue widgets in some implementations (unless the description makes clear that the system includes only one blue widget).

X. General Terms and Phrases

Throughout this specification, some of the following terms and phrases are used.

Bus according to some embodiments: Generally speaking, a bus is a communication system that transfers information between components inside a computer system, or between computer systems. A processor or a particular system (e.g., the processor 454 of the server 450) or subsystem may communicate with other components of the system or subsystem (e.g., the components 452 and 456) via one or more communication links. When communicating with components in a shared housing, for example, the processor may be communicatively connected to components by a system bus. Unless stated otherwise, as used herein the phrase "system bus" and the term "bus" refer to: a data bus (for carrying data), an address bus (for determining where the data should be sent), a control bus (for determining the operation to execute), or some combination thereof. Depending on the context, "system bus" or "bus" may refer to any of several types of bus structures including a memory bus or memory controller, a peripheral bus, or a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus.

Communication Interface according to some embodiments: Some of the described devices or systems include a "communication interface" (sometimes referred to as a "network interface"). A communication interface enables the system to send information to other systems and to receive information from other systems, and may include circuitry for wired or wireless communication.

Each described communication interface or communications unit (e.g., communications unit 160) may enable the device of which it is a part to connect to components or to other computing systems or servers via any suitable network, such as a personal area network (PAN), a local area network (LAN), or a wide area network (WAN). In particular, the communication unit 160 may include circuitry for wirelessly connecting the smart ring 101 to the user device 104 or the network 105 in accordance with protocols and standards for NFC (operating in the 13.56 MHz band), RFID (operating in frequency bands of 125-134 kHz, 13.56 MHz, or 856 MHz to 960 MHZ), Bluetooth (operating in a band of 2.4 to 2.485 GHZ), Wi-Fi Direct (operating in a band of 2.4 GHz or 5 GHZ), or any other suitable communications protocol or standard that enables wireless communication.

Communication Link according to some embodiments: A "communication link" or "link" is a pathway or medium connecting two or more nodes. A link between two end-nodes may include one or more sublinks coupled together via one or more intermediary nodes. A link may be a physical link or a logical link. A physical link is the interface or medium(s) over which information is transferred, and may be wired or wireless in nature. Examples of physicals links may include a cable with a conductor for transmission of electrical energy, a fiber optic connection for transmission of light, or a wireless electromagnetic signal that carries information via changes made to one or more properties of an electromagnetic wave(s).

A logical link between two or more nodes represents an abstraction of the underlying physical links or intermediary nodes connecting the two or more nodes. For example, two or more nodes may be logically coupled via a logical link. The logical link may be established via any combination of physical links and intermediary nodes (e.g., routers, switches, or other networking equipment).

A link is sometimes referred to as a "communication channel." In a wireless communication system, the term "communication channel" (or just "channel") generally refers to a particular frequency or frequency band. A carrier signal (or carrier wave) may be transmitted at the particular frequency or within the particular frequency band of the channel. In some instances, multiple signals may be transmitted over a single band/channel. For example, signals may sometimes be simultaneously transmitted over a single band/channel via different sub-bands or sub-channels. As another example, signals may sometimes be transmitted via the same band by allocating time slots over which respective transmitters and receivers use the band in question.

Memory and Computer-Readable Media according to some embodiments: Generally speaking, as used herein the phrase "memory" or "memory device" refers to a system or device (e.g., the memory unit 144) including computer-readable media ("CRM"). "CRM" refers to a medium or media accessible by the relevant computing system for placing, keeping, or retrieving information (e.g., data, computer-readable instructions, program modules, applications, routines, etc.). Note, "CRM" refers to media that is non-transitory in nature, and does not refer to disembodied transitory signals, such as radio waves.

The CRM may be implemented in any technology, device, or group of devices included in the relevant computing system or in communication with the relevant computing system. The CRM may include volatile or nonvolatile media, and removable or non-removable media. The CRM may include, but is not limited to, RAM, ROM, EEPROM, flash memory, or other memory technology, CD-ROM, digital versatile disks (DVD) or other optical disk storage, magnetic cassettes, magnetic tape, magnetic disk storage or other magnetic storage devices, or any other medium which can be used to store information, and which can be accessed by the computing system. The CRM may be communicatively coupled to a system bus, enabling communication between the CRM and other systems or components coupled to the system bus. In some implementations the CRM may be coupled to the system bus via a memory interface (e.g., a memory controller). A memory interface is circuitry that manages the flow of data between the CRM and the system bus.

Network according to some embodiments: As used herein and unless otherwise specified, when used in the context of system(s) or device(s) that communicate information or data, the term "network" (e.g., the networks 105 and 440) refers to a collection of nodes (e.g., devices or systems capable of sending, receiving or forwarding information) and links which are connected to enable telecommunication between the nodes.

Each of the described networks may include dedicated routers responsible for directing traffic between nodes, and, optionally, dedicated devices responsible for configuring and managing the network. Some or all of the nodes may be also adapted to function as routers in order to direct traffic sent between other network devices. Network devices may be inter-connected in a wired or wireless manner, and network devices may have different routing and transfer capabilities. For example, dedicated routers may be capable of high volume transmissions while some nodes may be capable of sending and receiving relatively little traffic over the same period of time. Additionally, the connections between nodes on a network may have different throughput capabilities and different attenuation characteristics. A fiberoptic cable, for example, may be capable of providing a bandwidth several orders of magnitude higher than a wireless link because of the difference in the inherent physical limitations of the medium. If desired, each described network may include networks or sub-networks, such as a local area network (LAN) or a wide area network (WAN).

Node according to some embodiments: Generally speaking, the term "node" refers to a connection point, redistribution point, or a communication endpoint. A node may be any device or system (e.g., a computer system) capable of sending, receiving or forwarding information. For example, end-devices or end-systems that originate or ultimately receive a message are nodes. Intermediary devices that receive and forward the message (e.g., between two end-devices) are also generally considered to be "nodes."

Processor according to some embodiments: The various operations of example methods described herein may be performed, at least partially, by one or more processors (e.g., the one or more processors in the processor unit 142). Generally speaking, the terms "processor" and "microprocessor" are used interchangeably, each referring to a computer processor configured to fetch and execute instructions stored to memory. By executing these instructions, the processor(s) can carry out various operations or functions defined by the instructions. The processor(s) may be temporarily configured (e.g., by instructions or software) or permanently configured to perform the relevant operations or functions (e.g., a processor for an Application Specific Integrated Circuit, or ASIC), depending on the particular embodiment. A processor may be part of a chipset, which may also include, for example, a memory controller or an I/O controller. A chipset is a collection of electronic components in an integrated circuit that is typically configured to provide I/O and memory management functions as well as a plurality of general purpose or special purpose registers, timers, etc. Generally speaking, one or more of the described processors may be communicatively coupled to other components (such as memory devices and I/O devices) via a system bus.

The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

Words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

Although specific embodiments of the present disclosure have been described, it will be understood by those of skill in the art that there are other embodiments that are equivalent to the described embodiments. Accordingly, it is to be understood that the present disclosure is not to be limited by the specific illustrated embodiments.

What is claimed is:

1. A system for displaying information via a smart ring comprising:
   a ring band configured to be worn on a finger of a user;
   a processor disposed within the ring band and configured to:
      receive an identification of the user of the smart ring;
      receive data from one or more of:
         a communication module within the ring band, or
         a sensor within the ring band; and
   a display (a.1) disposed at least partially in, (a.2) disposed at least partially on, or (a.3) coupled to the ring band and (b) communicatively coupled to the processor, wherein the processor is configured to:
      activate the display in a pattern indicative of the identification of the user to provide permissions to the user.

2. The system for displaying the information via the smart ring of claim 1, wherein:
   the display is configured to present a condition identified by the smart ring, wherein the condition is a biometric condition of the user.

3. The system for displaying the information via the smart ring of claim 1, wherein:
   the display is configured to present a condition identified by the smart ring, wherein the condition is a vehicular status or a vehicular operation.

4. The system for displaying the information via the smart ring of claim 1, wherein:
   the display is configured to present a color depending on a condition, as identified.

5. The system for displaying the information via the smart ring of claim 1, wherein:
   the processor communicates with a device to obtain a status of a vehicle.

6. The system for displaying the information via the smart ring of claim 1, wherein the pattern of the display comprises:
   a sequential illumination depending on the identification of the user.

7. The system for displaying the information via the smart ring of claim 1, wherein:
   the display is configured to present a message depending on a condition, as identified.

8. The system for displaying the information via the smart ring of claim 1, wherein:
   the display is configured to scroll to a message depending on a condition, as identified.

9. The system for displaying the information via the smart ring of claim 1, wherein:
   the processor configured to identify the user of the smart ring is further configured to unlock a door depending on a confirmed identification of the user.

10. A method of displaying information via a smart ring comprising:

by a processor disposed within a ring band of the smart ring:

receiving an identification of a user of the smart ring;

receiving data from one or more of:

a communication module within the ring band, or a sensor within the ring band; and presenting the information via a display (a.1) disposed at least partially in, (a.2) disposed at least partially on, or (a.3) coupled to the ring band and (b) communicatively coupled to the processor, wherein:

the ring band is configured to be worn on a finger of the user; and the processor is configured to:

activate the display in a pattern indicative of the identification of the user to provide permissions to the user.

11. The method of displaying the information via the smart ring of claim 10, wherein:

the display is configured to present a condition identified by the smart ring, wherein the condition is a biometric condition of the user.

12. The method of displaying the information via the smart ring of claim 10, wherein:

the processor communicates with a device to obtain a status of a vehicle.

13. The method of displaying the information via the smart ring of claim 10, wherein:

the display is configured to present a message depending on a condition, as identified.

14. The method of displaying the information via the smart ring of claim 10, wherein:

the processor configured to identify the user of the smart ring is further configured to unlock a door depending on a confirmed identification of the user.

15. One or more non-transitory computer-readable media comprising computing instructions that, when executed on one or more processors, cause the one or more processors to perform operations comprising:

by a processor of the one or more processors disposed within a ring band of a smart ring:

receiving an identification of a user of the smart ring;

receiving data from one or more of:

a communication module within the ring band, or a sensor within the ring band; and presenting information via a display (a.1) disposed at least partially in, (a.2) disposed at least partially on, or (a.3) coupled to the ring band and (b) communicatively coupled to the processor, wherein:

the ring band is configured to be worn on a finger of the user; and the processor is configured to:

activate the display in a pattern indicative of the identification of the user to provide permissions to the user.

16. The one or more non-transitory computer-readable media of claim 15, wherein:

the display is configured to present a condition identified by the smart ring, wherein the condition is a vehicular status or a vehicular operation.

17. The one or more non-transitory computer-readable media of claim 15, wherein:

the display is configured to present a color depending on a condition, as identified.

18. The one or more non-transitory computer-readable media of claim 15, wherein the pattern of the display comprises:

a sequential illumination depending on the identification of the user.

19. The one or more non-transitory computer-readable media of claim 15, wherein:

the display is configured to present a message depending on a condition, as identified.

20. The one or more non-transitory computer-readable media of claim 15, wherein:

the display is configured to scroll to a message depending on a condition, as identified.

* * * * *